US011318198B2

(12) United States Patent
Hashem

(10) Patent No.: US 11,318,198 B2
(45) Date of Patent: *May 3, 2022

(54) MERS-COV VACCINE COMPOSITION

(71) Applicant: King Abdulaziz University, Jeddah (SA)

(72) Inventor: Anwar M. Hashem, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/484,557

(22) Filed: Sep. 24, 2021

(65) Prior Publication Data

US 2022/0008530 A1    Jan. 13, 2022

Related U.S. Application Data

(60) Continuation of application No. 17/230,309, filed on Apr. 14, 2021, now Pat. No. 11,154,612, which is a division of application No. 17/101,572, filed on Nov. 23, 2020, which is a division of application No. 16/201,409, filed on Nov. 27, 2018, now Pat. No. 10,849,972.

(51) Int. Cl.
| | |
|---|---|
| *A61K 39/00* | (2006.01) |
| *A61K 39/215* | (2006.01) |
| *A61K 39/12* | (2006.01) |
| *C07K 14/705* | (2006.01) |
| *C12N 7/00* | (2006.01) |
| *A61P 31/14* | (2006.01) |
| *C12N 15/62* | (2006.01) |

(52) U.S. Cl.
CPC ............ *A61K 39/215* (2013.01); *A61P 31/14* (2018.01); *C07K 14/70575* (2013.01); *C12N 15/62* (2013.01)

(58) Field of Classification Search
CPC .. A61K 39/12; A61K 39/215; A61K 2039/53; A61P 31/14; C12N 2770/20034
See application file for complete search history.

(56) References Cited

U.S. PATENT DOCUMENTS

| | | |
|---|---|---|
| 9,884,895 B2 | 2/2018 | Baric et al. |
| 9,889,194 B2 | 2/2018 | Jiang et al. |
| 2016/0264647 A1 | 9/2016 | Dimitrov et al. |

FOREIGN PATENT DOCUMENTS

| | | |
|---|---|---|
| WO | 2016/090345 A1 | 6/2016 |
| WO | 2018/115527 A2 | 6/2018 |

OTHER PUBLICATIONS

Du, et al. ; Identification of a Receptor-Binding Domain in the S Protein of the Novel Human Coronavirus Middle East Respiratory Syndrome Coronavirus as an Essential Target for Vaccine Development ; Journal of Virology, vol. 87 (17) ; pp. 9939-9942 ; Sep. 2013 ; 4 Pages.

Chi, et al. ; DNA Vaccine Encoding Middle East Respiratory Syndrome Coronavirus S1 Protein Induces Protective Immune Responses in Mice ; HHS Public Access, Vaccine vol. 35 (16) ; pp. 2069-2075 ; Apr. 11, 2017 ; 16 Pages.

Tai, et al. ; A recombinant receptor-binding domain of MERS-CoV in trimeric form protects human dipeptidyl peptidase 4(hDPP4) transgenic mice from MERS-CoV infection ; Virology 499 ; pp. 375-382 ; 2016 ; 8 Pages.

*Primary Examiner* — Barry A Chestnut
(74) *Attorney, Agent, or Firm* — Oblon, McClelland, Maier & Neustadt, L.L.P.

(57) ABSTRACT

An immunogenic CD40-targeted trimeric MERS-CoV S1 fusion polypeptide as well as a corresponding polynucleotide encoding it and its use for safely inducing immune responses directed against MERS-CoV without inducing vaccine associated respiratory pathologies associated with non-targeted vaccines.

7 Claims, 10 Drawing Sheets

Specification includes a Sequence Listing.

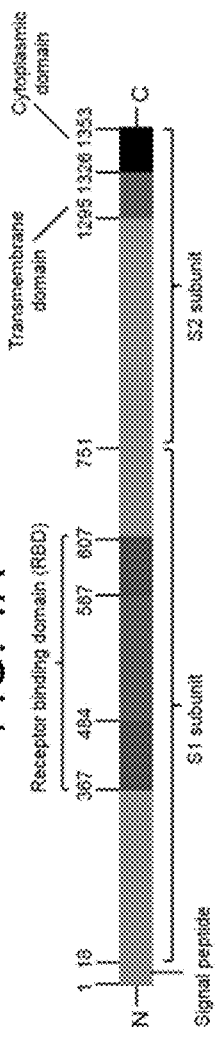
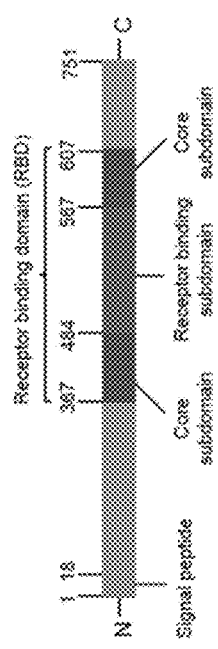

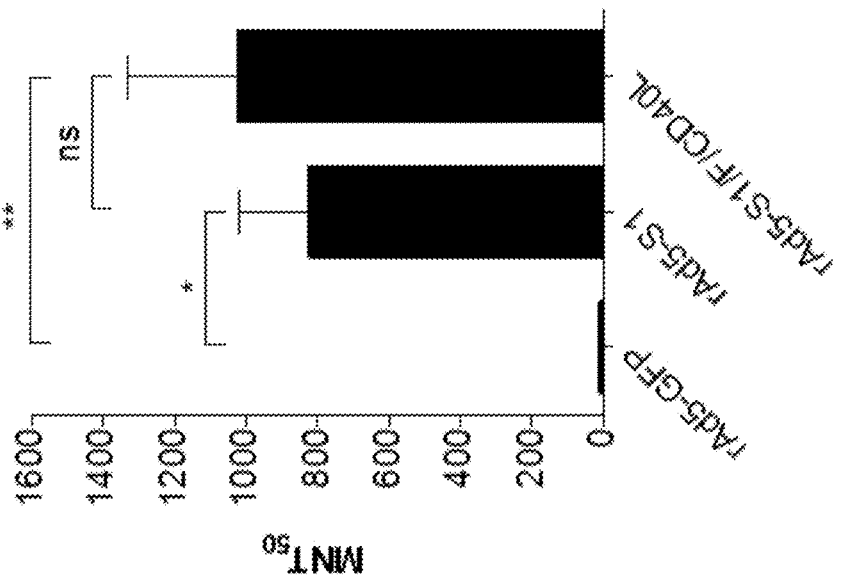
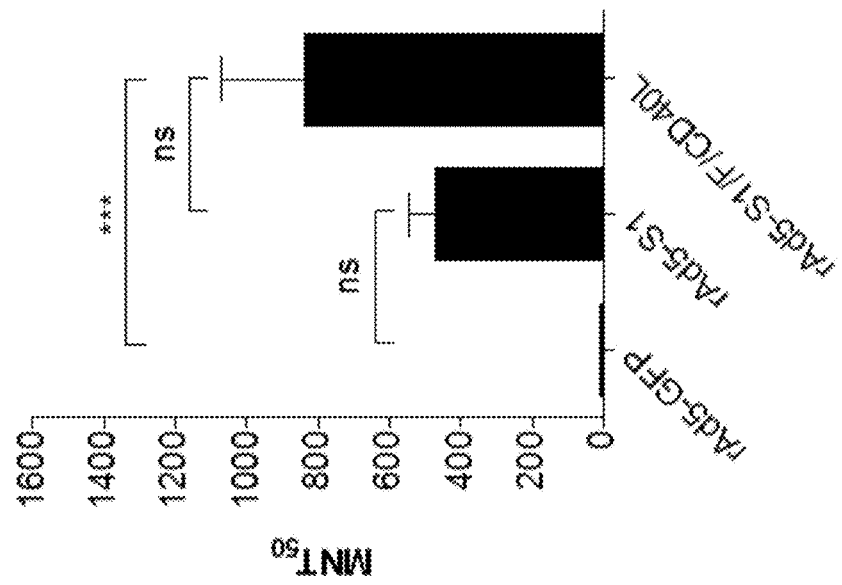

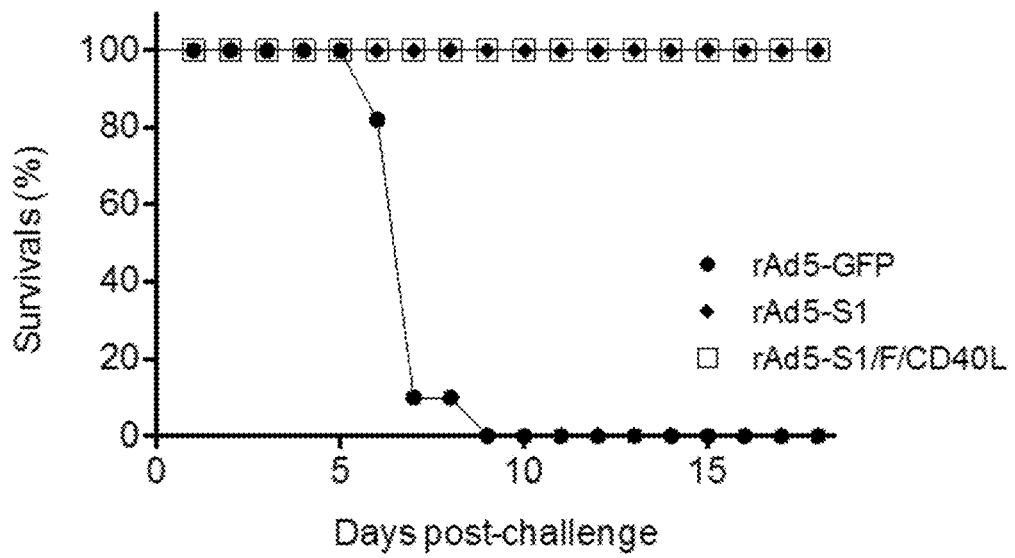
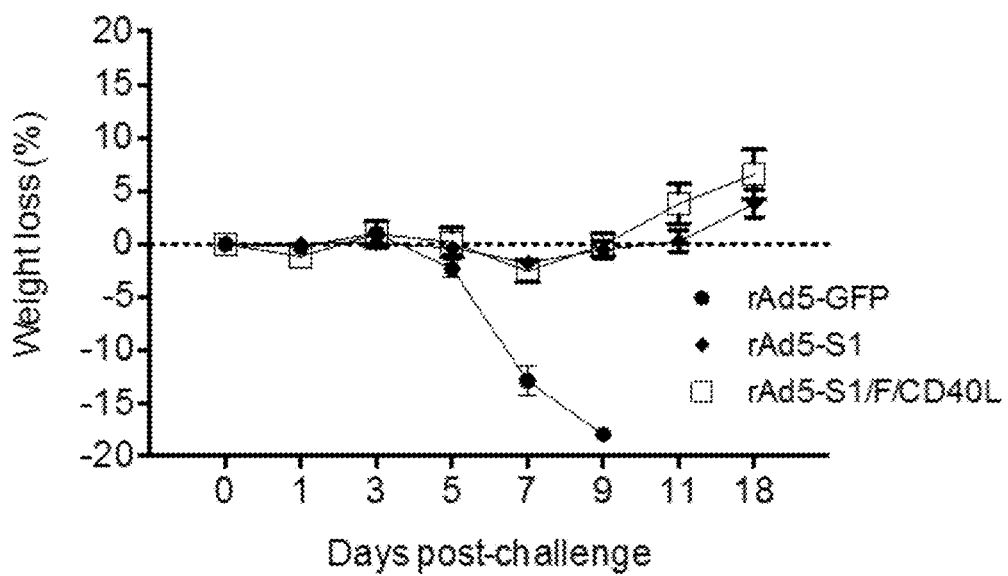

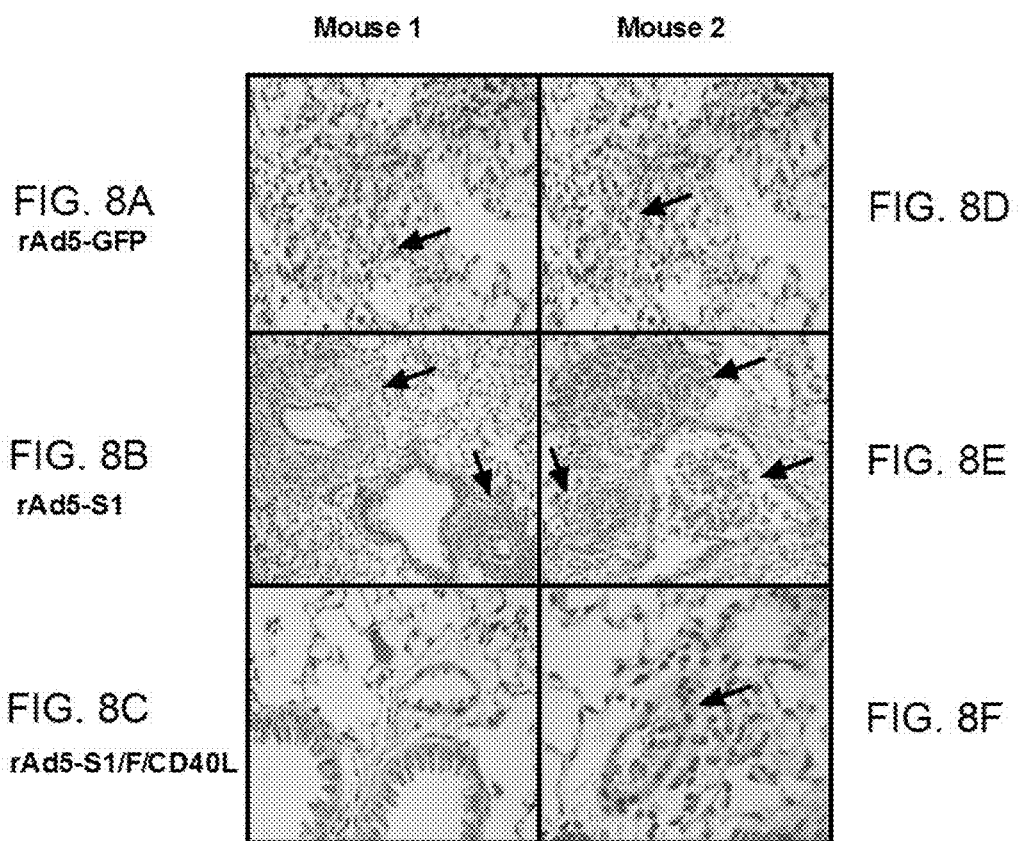

MERS-COV VACCINE COMPOSITION

CROSS-REFERENCE TO RELATED APPLICATION

The present application is a Continuation of U.S. application Ser. No. 17/230,309, now allowed, having a filing date of Apr. 14, 2021, which is a Division of U.S. application Ser. No. 17/101,572, having a filing date of Nov. 23, 2020, which is a Division of U.S. application Ser. No. 16/201,409, now U.S. Pat. No. 10,849,972, having a filing date of Nov. 27, 2018.

BACKGROUND

Field of the Invention

The invention falls within the fields of molecular virology, immunology and medicine.

Description of the Related Art

The "background" description provided herein is for the purpose of generally providing a context of the disclosure. Work of the presently named inventor, to the extent it is described in this background section as well as aspects of the description which may not otherwise qualify as prior art at the time of filing are neither expressly or impliedly admitted as prior art against the present invention.

The Middle East respiratory syndrome coronavirus (MERS-CoV) is a recently emergent zoonotic virus that was first isolated from a fatal human infection in Saudi Arabia in 2012; Zaki, A. M. et al. *Isolation of a novel coronavirus from a man with pneumonia in Saudi Arabia*. N. Engl. J. Med. 367, 1814-1820 (2012).

This zoonotic virus causes a variety of clinical manifestations in humans ranging from asymptomatic or mild infections to severe acute and fatal respiratory symptoms associated with fever, cough, acute pneumonia, shortness of breath, systemic infection and occasional multi-organ failure; Zaki et al., id. (2012).

As of January 2018, MERS-CoV has caused more than 2,143 laboratory-confirmed infections in 27 countries with a 30-40% mortality rate; Saudi Arabia is the most affected country; World Health Organization. *Middle East respiratory syndrome coronavirus (MERS-CoV)—Saudi Arabia*. Disease outbreak news 26 Jan. 2018 (hypertext transfer protocol://worldwideweb.who.int/csr/don/26-january-2018-mers-saudi-arabia/en/).

Most MERS-CoV cases have been linked to local infections or transmissions that occur in countries within the Arabian Peninsula where MERS-CoV has been endemic for more than six years. However, MERS-CoV has the potential to spread globally as apparent from a 2015 outbreak in South Korea; Park, S. H. et al. *Outbreaks of Middle East Respiratory Syndrome in Two Hospitals Initiated by a Single Patient in Daejeon*, South Korea. Infect. Chemother. 48, 99-107 (2016).

Countries in or near the Arabian Peninsula with laboratory-confirmed MERS cases include Bahrain, Iran, Jordan, Kuwait, Lebanon, Oman, Qatar, Saudi Arabia, United Arab Emirates (UAE), and Yemen. Countries outside the Arabian peninsula with travel-related MERS-CoV infections include Algeria, Austria, China, Egypt, France, Germany, Greece, Italy, Malaysia, Netherlands, Philippines, Republic of Korea, Thailand, Tunisia, Turkey, United Kingdom (UK), and the United States of America (USA) hypertext transfer protocol secure://worldwideweb.cdc.gov/coronavirus/mers/index.html, last accessed Aug. 17, 2018, incorporated by reference).

According to the World Health Organization (WHO) people at increased risk of MERS-CoV infection include those who live in or travel to the Arabian peninsula, those in close contact with a person exposed to or infected with MERs-CoV, and those in close contact with cameloids or cameloid products such as camel meat or milk. People at risk for severe MERS-CoV infection include those with diabetes, kidney failure, or chronic lung disease, and people who have weakened immune systems (hypertext transfer protocol secure://worldwideweb.cdc.gov/coronavirus/mers/risk.htm (last accessed, Aug. 17, 2018; incorporated by reference).

MERS-CoV is a lineage C betacoronavirus and is closely related to bat CoVs (HKU4 and HKU5); Zaki et al.; and Memish, Z. A. et al. *Middle East respiratory syndrome coronavirus in bats, Saudi Arabia*. Emerg. Infect. Dis. 19, 1819-1823 (2013). Several lines of evidence suggest that insectivorous bats are the original source of MERS-CoV and that MERS-CoV might have emerged via genetic recombination events; Memish et al.; Cotten, M. et al. *Full-genome deep sequencing and phylogenetic analysis of novel human betacoronavirus*. Emerg. Infect. Di s. 19, 736 (2013); Corman, V. M. *Rooting the phylogenetic tree of MERS-Coronavirus by characterization of a conspecific virus from an African Bat*. J. Virol. 88, 11297-11303 (2014); and Anthony, S. J. et al. *Further Evidence for Bats as the Evolutionary Source of Middle East Respiratory Syndrome Coronavirus*. MBio. 8, e00373-17 (2017). However, due to the limited direct contact between humans and bats, it is unlikely that bats are a source of primary human infection.

Molecular and serological epidemiological studies have shown a widespread detection of MERS-CoV in dromedary camels in the Arabian Peninsula and Africa suggesting that dromedaries are natural reservoirs of MERS-CoV or at least an important vector in its transmission to humans; Perera, R. A. et al. *Seroepidemiology for MERS coronavirus using microneutralisation and pseudoparticle virus neutralisation assays reveal a high prevalence of antibody in dromedary camels in Egypt*, June 2013. Euro. Surveill. 18, pii=20574 (2013); Reusken, C. B. et al. *Middle East respiratory syndrome coronavirus neutralising serum antibodies in dromedary camels: a comparative serological study*. Lancet Infect Dis. 13, 859-866 (2013); Meyer, B. et al. *Antibodies against MERS coronavirus in dromedary camels, United Arab Emirates*, 2003 and 2013. Emerg. Infect. Dis. 20, 552-559 (2014); Alagaili, A. N. et al. *Middle East respiratory syndrome coronavirus infection in dromedary camels in Saudi Arabia*. MBio. 5, pii:e00884-14 (2014); and Azhar, E. I. et al. *Evidence for camel-to-human transmission of MERS coronavirus*. N. Engl. J. Med. 370, 2499-2505 (2014).

The Middle East respiratory syndrome-related coronavirus (MERS-CoV), is a novel positive-sense, single-stranded RNA virus of the genus *Betacoronavirus*. HCoV-EMC/2012 or Human Coronavirus Erasmus Medical Center/2012 (Accession/version: JX869059.2) is the name of a novel strain of coronavirus first isolated from the sputum of an infected person. It was later named Middle East respiratory syndrome coronavirus or MERS-CoV. The polynucleotide sequences, locations of genes, coding sequences, and ORFs, and corresponding polypeptide sequences of MERS-CoV are incorporated by reference to the accession/version number above.

Unlike SARS-CoV, another coronavirus pathogen which uses human angiotensin-converting enzyme 2 (ACE2) as its receptor for binding to ACE2-expressing cells, MERS-CoV utilizes a different receptor, dipeptidyl peptidase 4 (DPP4) for binding to DPP4-expressing cells via its Spike protein.

Spike protein is a type I membrane protein that is expressed as a trimer on the virus' surface. It typically has 1353 amino acid residues and is made up of S1 and S2 subunits. The globular S1 subunit (residues 1-751) mediates virus binding to the DPP4 host cell receptor via its receptor binding domain (RBD). The RBD is typically designated as amino acid residues 367-606. The S2 subunit (residues 752-1353) contains an external domain, a transmembrane domain and a cytoplasmic domain, and mediates virus-cell membrane fusion as shown by FIG. 1; Lu, G. et al. *Molecular basis of binding between novel human coronavirus MERS-CoV and its receptor CD26*. Nature. 500, 227-231 (2013); and Raj, V. S. et al. *Dipeptidylpeptidase 4 is a functional receptor for the emerging human coronavirus—EMC*. Nature. 495, 251-254 (2013).

MERS-CoV RBD consists of a core subdomain and a receptor-binding motif (RBM) (receptor binding subdomain) (residues 484 to 567) which contains the motif and key residues to bind DPP4 receptor on the host cell membrane.

The core subdomain is composed of five-stranded antiparallel β sheets (β1, β2, β3, β4 and β9) with two short a helices. The receptor-binding subdomain is a four-stranded antiparallel β sheet (β5, β6, β7 and β8), located between strands β4 and β9 of the core subdomain. A total of 14 residues of MERS-CoV contact with 15 residues of the DPP4; Wang N, Shi X, Jiang L, et al. Structure of MERS-CoV spike receptor-binding domain complexed with human receptor DPP4. Cell Res. 2013 August; 23(8):986-93. doi: 10.1038/cr.2013.92; Chen Y, Rajashankar K R, Yang Y, et al. Crystal structure of the receptor-binding domain from newly emerged Middle East respiratory syndrome coronavirus. J Virol 2013; 10777-83. 27.

In other coronaviruses, such as SARS-CoV, the S protein has been shown to be the main target for host immune responses and a target for SARS vaccines that led to robust induction of neutralizing antibodies (nAbs)-mediated protection in immunized animals; He, Y. et al. *Receptor-binding domain of SARS-CoV spike protein induces highly potent neutralizing antibodies: implication for developing subunit vaccine*. Biochem. Biophys. Res. Commun. 324, 773-781 (2004); He, Y. et al. *Identification and characterization of novel neutralizing epitopes in the receptor binding domain of SARS-CoV spike protein: revealing the critical antigenic determinants in inactivated SARS-CoV vaccine*. Vaccine. 24, 5498-5508 (2006); and Du, L. et al. *The spike protein of SARS-CoV—a target for vaccine and therapeutic development*. Nat Rev Microbiol. 7, 226-236 (2009).

Likewise, the MERS-CoV S protein has been a focus for many MERS-CoV vaccine candidates. Several vaccine candidates based on full-length or truncated S protein including vectored vaccines, DNA vaccines, nanoparticle vaccines, S or RBD protein-based subunit vaccines and whole inactivated vaccines (WIV) have been developed and investigated in animal models; Wang, L. et al. *Evaluation of candidate vaccine approaches for MERS-CoV*. Nat. Commun. 6, 7712 (2015); Muthumani, K. et al. *A synthetic consensus anti-spike protein DNA vaccine induces protective immunity against Middle East respiratory syndrome coronavirus in nonhuman primates*. Sci. Transl. Med. 7, 301ra132 (2015); Coleman, C. M. et al. *Purified coronavirus spike protein nanoparticles induce coronavirus neutralizing antibodies in mice*. Vaccine. 32, 3169-3174 (2014); Du, L. et al. *A truncated receptor-binding domain of MERS-CoV spike protein potently inhibits MERS-CoV infection and induces strong neutralizing antibody responses: implication for developing therapeutics and vaccines*. PLoS. One. 8, e81587 (2013); Al-Amri, S. S. et al. *Immunogenicity of Candidate MERS-CoV DNA Vaccines Based on the Spike Protein*. Sci Rep. 7, 44875 (2017); Ma, C. et al. *Searching for an ideal vaccine candidate among different MERS coronavirus receptor-binding fragments—the importance of immunofocusing in subunit vaccine design*. Vaccine. 32, 6170-6176 (2014); Song, F. et al. *Middle East respiratory syndrome coronavirus spike protein delivered by modified vaccinia virus Ankara efficiently induces virus-neutralizing antibodies*. J. Virol. 87, 11950-11954 (2013); Haagmans, B. L. et al. *An orthopoxvirus-based vaccine reduces virus excretion after MERS-CoV infection in dromedary camels*. Science. 351, 77-81 (2016); Guo, X. et al. *Systemic and mucosal immunity in mice elicited by a single immunization with human adenovirus type 5 or 41 vector-based vaccines carrying the spike protein of Middle East respiratory syndrome coronavirus*. Immunology. 145, 476-484 (2015); Kim, E. et al. *Immunogenicity of an adenoviral-based Middle East Respiratory Syndrome coronavirus vaccine in BALB c mice*. Vaccine. 32, 5975-5982 (2014); Alharbi, N. K. et al. *ChAdOx1 and MVA based vaccine candidates against MERS-CoV elicit neutralising antibodies and cellular immune responses in mice*. Vaccine. 35, 3780-3788 (2017); and Agrawal, A. S. et al. *Immunization with inactivated Middle East Respiratory Syndrome coronavirus vaccine leads to lung immunopathology on challenge with live virus*. Hum. Vaccin. Immunother. 12, 2351-2316 (2016).

Various MERS-CoV vaccine platforms to combat MERS-CoV have been investigated. Most of these experimental vaccines were based on MERS-CoV full-length or truncated versions of the spike protein; these prototype vaccines induced high levels of nAb (neutralizing antibody) and sometimes conferred complete protection against MERS-CoV challenge in several animal models. However, serious safety concerns are associated with vaccines for several CoVs including SARS-CoV and MERS-CoV including inflammatory and immunopathological effects such as eosinophilic infiltration of the lungs as well as Ab-mediated disease enhancement (ADE) in immunized animals upon viral challenge. Some of these side-effects are shared with vaccines to other coronaviruses; Agrawal, et al., id.; Weingartl, H. et al. *Immunization with MVA-based recombinant vaccine against SARS is associated with enhanced hepatitis inferrets*. J. Virol. 78, 12672-12676 (2004); Tseng, C. T. et al. *Immunization with SARS coronavirus vaccines leads to pulmonary immunopathology on challenge with the SARS virus*. PloS One. 7, e35421 (2012); Yang, Z. Y. et al. *Evasion of antibody neutralization in emerging severe acute respiratory syndrome coronaviruses*. Proc. Natl. Acad. Sci. USA. 102, 797-801 (2005); Czub, M., Weingartd, H., Czub, S., He, R. & Cao, J. *Evaluation of modified vaccinia virus ankara based recombinant SARS vaccine in ferrets*. Vaccine. 23, 2273-2279 (2005); Deming, D. et al. *Vaccine efficacy in senescent mice challenged with recombinant SARS-CoV bearing epidemic and zoonotic spike variants*. PLoS Med. 3, 2359-75 (2006); Olsen, C. W., Corapi, W. V., Ngichabe, C. K., Baines, J. D. & Scott, F. W. *Monoclonal antibodies to the spike protein of feline infectious peritonitis virus mediate antibody-dependent enhancement of infection of feline macrophages*. J. Virol. 66, 956-965 (1992); Jaume, M. et al. *SARS CoV subunit vaccine: Antibody-mediated neutralisation and enhancement*. Hong Kong Med. J. 18 Suppi 2, 31-36 (2012); Weiss, R. C. & Scott, F. W. *Antibody-mediated enhancement of disease in feline infectious peritonitis: Comparisons with dengue hemorrhagic fever*. Comp. Immunol. Microbiol. Infect Dis. 4, 175-189 (1981), each incorporated herein by reference in their entirety.

The inventor considered that induction of antibodies that do not neutralize MERS-CoV could increase the risk of undesired inflammatory or immunological side-effects while having little or no effect on virus attachment. This is because epitopes outside of the S1 RBD of MERS-CoV could induce anti-virus immune responses that do not block attachment and entry of the virus into a host cell but which contribute to undesired inflammatory phenomena. Thus, use of a neutralizing epitope-rich S1 region was considered an attractive target for effective and safe MERS vaccine that blocks virus entry into host cells; Olsen et al., id.; Jaume et al., id.; and Weiss et al., id. However, even immune responses to S1 antigen may induce undesired side-effects.

Consequently, the inventor investigated whether targeting S1 antigen to a subset of antigen presenting cells could reduce undesirable immune responses to S1 and other Mers-CoV antigens while inducing a robust response against key portions of MERS-CoV involved in the host-parasite interaction.

CD40 is a receptor constitutively expressed on many antigen presenting cells. A ligand that binds to CD40 is CD40 Ligand or CD40L. CD40L is a costimulatory molecule that is an essential regulator of the immune system. Structurally CD40L is a type II membrane that is expressed on activated $CD4^+$ T cells and some other antigen presenting cells typically in a transient fashion; van Kooten, C. & Banchereau, J. *CD40-CD40 ligand.* J. Leukoc. Biol. 67, 2-17 (2000); and Ma, D. Y. & Clark, E. A. *The role of CD40 and CD154 CD40L in dendritic cells.* Sem. Immunol. 21, 265-272 (2009). Other ligands for CD40 that may be employed along with or instead of CD40L include antibodies or antibody fragments that activate or agonize CD40 including monoclonal antibodies and their fragments or chimeric or fully human antibodies to CD40 and their fragments, as well as other CD40 agonists or other molecules that crosslink CD40, including biosimilars of the aforementioned agents.

Based on the study of mutations in CD40 or CD40L genes in both animals and humans, CD40L and its receptor CD40 together form a crucial link between innate and adaptive immunity; van Kooten et al; Ma et al.; Bishop, G. A. & Hostager, B. S. *The CD40-CD154 interaction in B cell-T cell liaisons.* Cytokine Growth Factor Rev. 14, 297-309 (2003); Fujii, S. I., Liu, K., Smith, C., Bontio, A. J. & Steinman, R. M. *The linkage of innate to adaptive immunity via maturing dendritic cells in vivo requires CD40 ligation in addition to antigen presentation and CD80/86 costimulation.* J. Exp. Med. 199, 1607-1618 (2004); Allen, R. C. et al. *CD40 ligand gene defects responsible for X-linked hyper-IgM syndrome.* Science. 259, 990-993 (1993); Kawabe, T. et al. *The immune responses in CD40-deficient mice: impaired immunoglobulin class switching and germinal center formation.* Immunity. 1, 167-178 (1994); and Renshaw, B. R. et al. *Humoral immune responses in CD40 ligand-deficient mice.* J. Exp. Med. 180, 1889-1900 (1994).

Use of CD40L as a molecular adjuvant has been investigated by several groups using multiple strategies such as co-delivery of CD40L along with an antigen or retargeting the delivery vectors to CD40 on APCs; Cao, J. et al. *CD40 ligand expressed in adenovirus can improve the immunogenicity of the GP3 and GP5 of porcine reproductive and respiratory syndrome virus in swine.* Vaccine. 28, 7514-7522 (2010); Gómez, C. E., Najera, J. L., Sanchez, R., Jimenez, V., & Esteban, M. *Multimeric soluble CD40 ligand (sCD40L) efficiently enhances HIV specific cellular immune responses during DNA prime and boost with attenuated poxvirus vectors MVA and NYVAC expressing HIV antigens.* Vaccine. 27, 3165-3174 (2009); Huang, D. et al. *Significant alterations of biodistribution and immune responses in Balb c mice administered with adenovirus targeted to CD40 (+) cells.* Gene Ther. 15, 298-308 (2007); Lin, F. C., Peng, Y., Jones, L. A., Verardi, P. H. & Yilma, T. D. *Incorporation of CD40 ligand into the envelope of pseudotyped single-cycle simian immunodeficiency viruses enhances immunogenicity.* J. Virol. 83, 1216-1227 (2009); Yao, Q. et al. *Immunogenicity and protective efficacy of a DNA vaccine encoding a chimeric protein of avian influenza hemagglutinin subtype H5 fused to CD154 (CD40L) in Pekin ducks.* Vaccine. 28, 8147-8156 (2010); Hashem, A. M. et al. *CD40 ligand preferentially modulates immune response and enhances protection against influenza virus.* J. Immunol. 193, 722-734 (2014); and Fan, X. et al. *Targeting the HA2 subunit of influenza A virus hemagglutinin via CD40L provides universal protection against diverse subtypes.* Mucosal Immunol. 8, 211-220 (2015), each incorporated herein by reference in their entirety.

The inventor previously developed a non-replicating recombinant adenovirus-5 (rAd5) vectored prototype vaccine in which secreted influenza viral proteins are targeted to CD40-expressing APCs using CD40L; Hashem et al., id.; and Fan et al., id. While viral vectors such as rAd are effective and immunogenic, they are often associated with safety problems. At least three groups have developed and examined different rAd vectored MERS-CoV vaccines; Guo et al; Kim et al; Alharbi, N. K. et al. *ChAdOx1 and MVA based vaccine candidates against MERS-CoV elicit neutralising antibodies and cellular immune responses in mice.* Vaccine. 35, 3780-3788 (2017); and Munster, V. J. et al. *Protective efficacy of a novel simian adenovirus vaccine against lethal MERS-CoV challenge in a transgenic human DPP4 mouse model.* NPJ Vaccines. 2, 28 (2017). However, these previous studies have focused on the immunogenicity and/or the protective efficacy of the resulting vaccines and have not addressed vaccine associated pathology especially those occurring after viral challenge.

In previous studies, while robust immune response and high levels of protection were observed using different MERS-CoV vaccine platforms, lung pathology was also noticed in vaccinated and challenged animals. These studies involved a variety of different MERS-CoV vaccines including high dosage DNA-based vaccines, RBD or modified vaccinia virus ankara (MVA) vaccines, or recombinant measles virus encoding MERS-CoV S protein vaccine; Muthumani et al.; Tai, W. et al. *A recombinant receptor-binding domain of MERS-CoV in trimeric form protects human dipeptidyl peptidase 4 (hDPP4) transgenic mice from MERS-CoV infection.* Virology. 499, 375-382 (2016); Volz, A. et al. *Protective Efficacy of Recombinant Modified Vaccinia Virus Ankara Delivering Middle East Respiratory Syndrome Coronavirus Spike Glycoprotein.* J. Virol. 89, 8651-8656 (2015); and Malczyk, A. H. et al. *A Highly Immunogenic and Protective Middle East Respiratory Syndrome Coronavirus Vaccine Based on a Recombinant Measles Virus Vaccine Platform.* J. Virol. 89, 11654-11667 (2015); Agrawal et al.; Weingartl et al.; Tseng et al.; As apparent from these prior studies, a way to protect against MERS-CoV while safely avoiding inducing severe lung pathology following immunization has yet to be developed.

In view of the limitations and problems with MERS-CoV vaccines, the inventor sought to develop a safe and efficacious vaccine for MERs-CoV that would safely provide durable, broad, potent and universal protection against MERS-CoV.

SUMMARY OF THE INVENTION

The invention involves an immunogenic CD40-targeted trimeric MERS-CoV S1 fusion polypeptide as well as a corresponding polynucleotide encoding it and its use for safely inducing immune responses directed against MERS-CoV without inducing vaccine associated respiratory pathologies associated with non-targeted vaccines.

BRIEF DESCRIPTION OF THE FIGURES

FIG. 1A. Schematic representation of MERS-CoV spike protein with both S1 and S2 subunits. N refers to amino-terminus and C refers to the carboxyl-terminus.

FIG. 1B. Schematic representation of MERS-CoV spike protein S1 subunit and N terminal signal peptide with no S2 subunit.

FIG. 6A MERS-CoV Spike rAd vaccine induced neutralizing antibodies (nAbs) after priming. $MNT_{50}$ denotes complete protection of 50% of Vero cells in a well.

FIG. 6B MERS-CoV Spike rAd vaccine induced nAbs after boost. Neutralization titers for FIGS. 6A and 6B were determined as the highest serum dilutions from each individual mouse that completely protected Vero E6 cells in at least 50% of the wells ($MNT_{50}$). Titers are shown as means from 15 mice per group s.d from one experiment. *P<0.001, P<0.01 and *P<0.05 (one-way ANOVA with Bonferroni's post-test).

FIG. 7A. Percent survival of mice after immunization and subsequent challenge with MERS-CoV. Immunization with S1-based rAd vaccine rAd5-S1 and S1-based CD40-targeted rAd5-S1/F/CD40L provided complete protection against lethal MERS-CoV challenge, while all control animals (rAd-5-GFP) died. Groups of hDPP4 Tg+ mice were immunized with two doses of 109 pfu of the indicated rAd constructs and challenged with 100 $LD_{50}$ of MERS-CoV (EMC2012 strain) 5 weeks post secondary immunization. Data are shown from one experiment with n=11 mice per treatment group.

FIG. 7B. Percentage body weight loss of two immunized groups compared to control group (rAd5-GFP) described in FIG. 7A.

FIGS. 8A-8F. Histological comparison of lung pathology on day three post-challenge after immunization with rAd5-GFP (control, FIGS. 8A and 8D), non-targeted rAd5-S1 (FIGS. 8B and 8E) and CD40-targeted rAd5-S1/F/CD40L (FIGS. 8C and 8F) and challenge with MERS-CoV. Histopathologic evaluation was performed on deparaffinized sections stained by routine hematoxylin-eosin (H&E) staining. Arrows indicate monocytic and lymphocytic infiltrates as well as perivascular hemorrhage.

DETAILED DESCRIPTION

Figure 2:
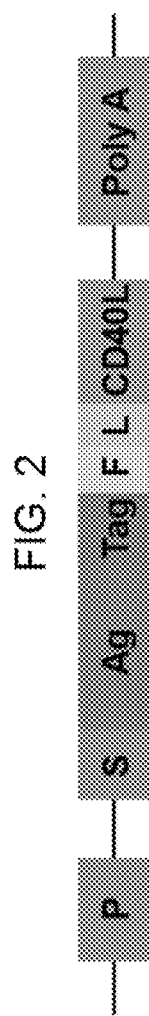
FIG. 2. Schematic representation of a chimeric nucleic acid encoding a prototype vaccine rAd5-S/Ag/F/CD40L. P: promoter such as a CMV promoter, S: leader sequence, Ag: coding sequence of antigen of interest, tag: affinity tag sequence for protein purification such as histidine tag, F: T4 bacteriophage fibritin trimerization motif sequence, L: Linker sequence (e.g., nonpolar amino acids), CD40L: ectodomain of CD40 ligand (CD40L), Poly A: polyadenylation tail.

Toward an objective of providing a safe and effective vaccine to MERS-CoV, the inventor engineered and tested a vaccine platform that targets MERS-CoV S1 antigen to CD40 expressed by antigen presenting cells. A vaccine containing the CD40 targeted S1 antigen (rAd5-S1/F/CD40L) was compared to an S1-based vaccine that did not target CD40 (rAd5-S1) and to a control vaccine without S1 (rAd5-GFP). Immunization of human DPP4 transgenic mice showed that a single dose of the targeted rAd5-S1/F/CD40L vaccine elicited highly significant levels of neutralizing antibodies compared to that produced by the non-CD40-targeted rAd5-S1 vaccine which required two doses to induce robust response. As shown by MERS-CoV challenge, both vaccines conferred complete protection against infection and resulted in undetectable infectious virus titers as well as significantly lower levels of viral RNA in the lungs as compared to the control. However, surprisingly, the mice immunized with the non-targeted S1 vaccine (rAd5-S1), but not those immunized with the CD40-targeted vaccine (rAd5-S1/F/CD40L), exhibited pulmonary perivascular hemorrhage three days post challenge despite the observed protection showing that immunization with S1 without CD40L targeting leads to vaccine-associated lung pathology after viral exposure.

These data indicate that using CD40L as a targeting molecule and molecular adjuvant not only enhances immunogenicity and protective efficacy against MERS-CoV but also prevents such pulmonary pathology. Moreover, the CD40-targeted vaccine was more potent suggesting that a lower dosage could be used further reducing the risk immunological side-effects. These results also show that immunization with a consensus S1 antigen sequence induces protective immune responses against MERS-CoV.

MERS-CoV antigens include viral antigens encoded by the structural protein genes Spike (S), Envelope (E), Membrane (M) and nucleopcapside (N). MERS-CoV also expresses a polymerase. Spike (S) protein is assembled into trimers which form peplomers on the surface of the viral particle that give the Coronaviridae family its name. Typically, an immunogen or vaccine containing a CD40-targeted polypeptide (a polypeptide that is directed or targeted to CD40 on antigen presenting cells) of the invention will only contain viral S protein, or only S1 protein epitopes, for example, it will omit epitopes from other MERS-CoV antigens and a S1-specific immunogen will omit S2 epitopes. However, in some embodiments, such a vaccine may substitute or include one or more other antigens or epitopes of non-S1 MERS-CoV antigens either as part of a CD40-targeted polypeptide or as a separate ingredient of an immunogenic composition or vaccine.

Coronavirus antigens. In addition to MERS-CoV, five other types of human coronaviruses are known. These are 229E (alpha coronavirus), NL63 (alpha coronavirus), OC43 (beta coronavirus), HKU1 (beta coronavirus) and SARS-CoV (the beta coronavirus that causes severe acute respiratory syndrome, or SARS). Viral proteins involved in recognition, attachment and invasion of human host cells from these other coronaviruses, such as coronavirus S proteins, may be substituted for the S or S1 protein of MERS-CoV in the polypeptide according to the invention. In combination with a CD40 ligand, these polypeptides may provide substantial immunity against coronaviruses and reduce the severity of side-effects associated with vaccination, such as vaccine-induced inflammation or immunological hypersensitivity to an exogenous antigen.

Animal coronaviruses include Infectious bronchitis virus (IBV) which causes avian infectious bronchitis; Porcine coronavirus (transmissible gastroenteritis coronavirus of pigs, TGEV); Bovine coronavirus (BCV), responsible for severe profuse enteritis in of young calves; Feline coronavirus (FCoV) causes mild enteritis in cats as well as severe Feline infectious peritonitis (other variants of the same virus); two types of canine coronavirus (CCoV) (one causing enteritis, the other found in respiratory diseases); Turkey coronavirus (TCV) causes enteritis in turkeys; Ferret enteric coronavirus causes epizootic catarrhal enteritis in ferrets; Ferret systemic coronavirus causes FIP-like systemic syndrome in ferrets; Pantropic canine coronavirus; porcine epidemic diarrhea virus (PED or PEDV), has emerged around the world. Its economic importance is as yet unclear, but shows high mortality in piglets. In some embodiments, the invention is directed to immunogenic polypeptides containing a ligand targeting CD40 and an S1 protein analog from another coronavirus which replaces the MERS-CoV S1 determinants in a CD40-targeted MERS-CoV S1 fusion proteins.

The platform disclosed herein can be used for other viruses instead of MERS-CoV. It could be used with any other viral antigen or fragment thereof, or variant thereof including but not limited to a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1, herpes simplex 2, varicella-zoster virus, cytomegalovirus (CMV), Epstein-Barr virus (EBV), flavivirus, foot and mouth disease virus, chikungunya virus, lassa virus, arenavirus, Nipah virus, Lassa virus or cancer causing virus.

Middle East respiratory syndrome coronavirus. Various strains of MERS-CoV viruses have been isolated. Isolates of MERS CoV are described by accession KF186567.1 and KT026454.1 which are incorporated by reference. Another commonly used strain is described by accession number JX869059.2 (Human betacoronavirus 2c EMC/2012) which is also incorporated by reference.

Some embodiments of the invention involve the use of polynucleotides or proteins encoded by polynucleotides of different isolates of MERS CoV or variants having 95, 96, 97, 98, 99, 99.5, 99.9, <100 or 100% sequence identity to the isolates identified by accession/version number KF186567.1, JX869059.2 or KT026454.1.

MERS S protein is a structural spike protein encoded by the MERS CoV genome. The S glycoprotein consists of a globular S1 domain at the N-terminal region (e.g., residues 1-725), followed by membrane-proximal S2 domain, a transmembrane domain and an intracellular domain as shown in FIG. 1A. Sequences of some kinds of S proteins are described by accession/version numbers AGN70962.1 and AKK52592.1.

Natural or synthetic variants of S protein and its S1 and S2 subunits are also encompassed by the invention. These include S, S1 or S2 protein variants that have amino acid sequences that are at least 98, 99, 99.5, 99.9, <100% identical or similar to the amino acid sequences described by the above accession/version numbers or to the consensus S1 amino acid sequence of SEQ ID NO: 2, which may be encoded by the polynucleotide sequence of SEQ ID NO: 1. Immunogenic fragments of S proteins are also included as well as receptor binding portions of the S1 protein including those described by FIG. 1B.

CD40 is a costimulatory protein found on antigen presenting cells and is required for their activation. In the macrophage, the primary signal for CD40 activation is IFN-7 from Th1 type CD4 T cells. The secondary signal is CD40L (CD154) on the T cell which binds CD40 on the macrophage cell surface. As a result, the macrophage expresses more CD40 and TNF receptors on its surface increasing its level of activation.

Activation results in the induction of potent microbicidal substances in the macrophage including reactive oxygen species and nitric oxide leading to the destruction of ingested microbes but which could also induce immunological side-effects. Surprisingly, the inventor found that CD40-based targeting of S1 protein to antigen presenting cells reduced vaccine-associated side-effects despite contact of CD40 on antigen presenting cells with a CD40 ligand.

Human CD40 reference nucleic acid sequences include NM_001250 (SEQ ID NO: 18), NM_001302753, NM_152854, NM_001322421, and NM_001322422, each of which is incorporated by reference along with the corresponding encoded polypeptides. For example, SEQ ID NO: 18 encodes the amino acid sequence for human CD40 described by SEQ ID NO: 19. Vaccines for administration to humans will generally encompass a CD40L or a CD40L variant that bind to human CD40, or a CD40L ligand or variant that binds to the CD40 of a non-human animal being vaccinated.

Camelid CD40 encoding polynucleotides are described by NCBI Reference Sequences: XM_010978627.1 and XM_010978624.1 (SEQ ID NO: 20). A camelid CD40 amino acid sequence is described by SEQ ID NO: 21. Vaccines for administration to camelids will generally encompass a CD40L or a CD40L variant that binds to a camelid CD40.

Additional CD40 sequence isoforms or homologs are known and publically available via PubMed or in other public polynucleotide or polypeptide databases such as at: hypertext transfer protocol secure://worldwideweb.ncbi.nlm.nih.gov/protein/?term=cd40 or to (hypertext transfer protocol://worldwideweb.ncbi.nlm.nih.gov/nuccore/?term=cd40 (both last accessed Aug. 27, 2018 and both incorporated by reference). Vaccines for administration to other animals besides humans and camelids will generally encompass a CD40L or a CD40L variant that bind to a corresponding CD40 molecule from the relevant species.

CD40L (CD40 Ligand, CD154) is a protein that is primarily expressed on activated T cells and is a member of the TNF superfamily of molecules. It binds to CD40 on antigen-presenting cells (APC), which leads to many effects depending on the target cell type. CD40L has three binding partners: CD40, a501 integrin and αIIbβ. CD40L is a type II membrane protein which exists as either cell-surface protein or secreted protein. The cell surface-attached protein consists of cytoplasmic domain (CD) at its N-terminus, transmembrane domain (TMD) and an extracellular domain (ECD) at its C-terminus. On the other hand, the soluble form is mainly the extracellular domains of CD40L missing both CD and TMD. As shwon in the Example, the inventor used a coding region of the soluble form/ECD as it is responsible for CD40 binding on APCs by deleting the CD and TMD coding regions.

A variety of different CD40L polynucleotide and polypeptide sequences are known from different animals including humans (NM_000074.2, NP000065.1, GenBank: BC071754.1, SEQ ID NO: 22), Arabian camels (XP_010993166.1, XM_010994864.1, SEQ ID NO: 24), Bactrian camels (XP010950821.1), wild Bactrian camels (XP006195602.1; NCBI Reference Sequence: XM_010952519.1; SEQ ID NO: 26), horses (AEB61022.1; XP005614588.1), cattle (XP024844321.1), bison (XP010851595.1), sheep (NP 001068569.1), goats (XP005700481.1), dogs (NP001002981.1), cats (NP001009298.1) and mice (NP_035746.2). Additional CD40L sequence homologs are known and publically available via PubMed or in other public polynucleotide or polypeptide databases such as at: (hypertext transfer protocol secure://worldwideweb.ncbi.nlm.nih.gov/protein/?term=cd40+ligand or to (hypertext transfer protocol secure://worldwideweb.ncbi.nlm.nih.gov/nuccore/?term=cd40+ligand (both last accessed Aug. 27, 2018 and both incorporated by reference). In some embodiments of the invention, a CD40L from a human or non-human animal will be incorporated into a fusion polypeptide as described herein. In some embodiments a variant CD40L sequence may be used. Variant CD40L amino acid sequences that bind to CD40 may be at least 70, 75, 80, 85, 90, 95, 96, 97, 98, 99, <100% identical or similar to the CD40L sequences disclosed herein.

Trimerization motif. The CD40-targeted S1 polypeptide of the invention includes a trimerization motif which facilitates or enables formation of a trimer of the monomeric CD40-targeted polypeptides. One such trimerization motif is described by a foldon sequence derived from T4 phage fibritin described in SEQ ID NO: 6 and encoded by the polynucleotide of SEQ ID NO: 5. This sequence when incorporated into a polypeptide can stabilize formation of a triple helix by the component protein monomers. Other trimerization motifs include those described by, and incorporated by reference to Kammerer, et al., PNAS 102(39): 13891-13896 or variants of the T4 phage fibritin sequence of SEQ ID NO: 6 which contain 1, 2, 3, 4, 5, 6, 7, 8, 9, or 10 amino acid deletions, substitutions, or insertions and which retain an ability to form trimers. CD40L and MERS-CoV S protein are both trimers. A trimerization motif may be used to connect the surface exposed region from MERS-CoV spike protein (i.e. S1) to the soluble from of CD40L. The inventor found that trimerization leads to targeting of S1 to CD40-expressing cells, increasing binding avidity to CD40 receptor, promoting APCs (such as DCs and macrophages) activation and maturation, and stabilization of native trimeric conformation of both S1 and CD40L, a property necessary for efficient CD40 binding and function. As shown herein, a short fibritin fragment (27 aa) may be sufficient for forming stable trimers of a biologically active recombinant fusion protein. In one alternative embodiment, a trimerization motif that facilitates trimerization of S or S1 and/or CD40L may be, respectively, omitted as monomeric or dimeric forms of S1 can exhibit immunological activity and monomeric or dimeric forms of CD40L can bind to CD40.

Linkers may be used next to one or more elements of the invention, including next to S1 protein sequences, tags (e.g., His tag), or CD40 ligand sequences to facilitate the functions of these elements, such as to enhance the ability of a His-tag to bind to a substrate or enhance the ability of CD40 ligand to bind to CD40 on an antigen presenting cell. Flexible, rigid, or cleavable linkers may be used. Fusion protein linkers are described by, and incorporated by reference to Chen, X., et al., Fusion protein linkers: Property, design and functionality, Adv. Drug Deliv. Rev. 65(10):1357-1369. One such linker is the non-polar amino acid linker described by SEQ ID NO: 8 and encoded by SEQ ID NO: 7, though other non-polar linkers may also be used. A linker may be a single amino acid residue or contain 2, 3, 4, 5, 6, 7, 8, 9, 10, 11, 12, 13, 14, 15, 16, 17, 18, 19, 20 or more amino acid residues, preferably alanine or other non-polar amino acid residues.

A signal peptide sequence may be incorporated into a CD40-targeted S1 fusion polypeptide at its N-terminus to traffic the polypeptide out of a cell in which it is expressed. Signal peptides are extremely heterogeneous and many prokaryotic and eukaryotic signal peptides are functionally interchangeable even between different species. The efficiency of protein secretion is determined by the signal peptide, see Kober L, Zehe C, Bode J (April 2013). *"Optimized signal peptides for the development of high expressing CHO cell lines"*. Biotechnol. Bioeng. 110 (4): 1164-73. doi:10.1002 bit.24776. PMID 23124363; von Heijne G (July 1985). *"Signal sequences: The limits of variation"*. J Mol Biol. 184 (1): 99-105. doi:10.1016/0022-2836(85)90046-4. PMID 4032478 both incorporated by reference.

As shown in the Example, a CD40-targeted S1 fusion protein was engineered to be secretable by deleting the cytoplasmic and transmembrane domains from both S protein and CD40L and by the addition of the human tyrosinase signal peptide. However, as shown below no signal peptide was maintained from S protein, but human tyrosinase signal peptide or IL2 signal sequence can used as well as longer or shorter signal peptide sequences. The presence of the signal peptide (secretory signal sequence) upstream of the fusion protein should render the fusion protein secretable from in vivo infected cells upon. Gene products with a secretion signal produced by adenovirus-infected cells would be secreted to increase the antigen load and expression in vivo. The secretory signal sequence directs the S1-CD40L fusion protein to compartments of the cell which cause the fusion protein to be secreted from the cell. The same is expected if using DNA vaccine or other delivery vectors. Once the fusion protein is secreted it will be targeted to CD40-expressing cells (APCs) to enhance the immune response.

A signal peptide, such as residues 1-18 of SEQ ID NO: 12, is used in some embodiments of the invention.

In other embodiments, one skilled in the art may select an appropriate signal peptide for use with the invention. Suitable signal protein sequences are known in the art for various kinds of host cells. For example, a signal peptide encoded by one of the vectors available in a commercial kit may be used, see for example, from the Mammalian Signal Peptide Vector Set; hypertext transfer protocol secure://worldwideweb.sigmaaldrich.com/catalog/product/sigma/pp2379?lang=en&re gion=US (incorporated by reference, last accessed Aug. 24, 2018).

In other embodiments, where it is not desired to secrete a CD40-targeted S1 fusion polypeptide, a signal peptide may be omitted and the polypeptide recovered by lysis of the host cell. Other mammalian expression sequences or vectors such as those described by hypertext transfer protocol secure://worldwideweb.sigmaaldrich.com/life-science/molecular-biology/cloning-and-expression/vector-systems/transient-expression.html (last accessed Aug. 24, 2018, incorporated by reference) may also be used.

Protein tags. In one embodiment, the CD40-targeted polypeptide of the invention comprises a His-tag (SEQ ID NO: 4) which can be encoded by the polynucleotide sequence of SEQ ID NO: 3. Such tags are known in the art and incorporated by reference to hypertext transfer protocol secure://en.wikipedia.org/wiki/Polyhistidine-tag (last accessed Aug. 24, 2018). This stretch of histidine residues incorporated into the CD40-targeted polypeptide permits it to be recovered by affinity purification, for example, by binding between histidine and a metal ion such as copper, nickel, zinc, or cobalt. As the metal ion, copper has the highest affinity, and the affinity decreases in the order of nickel, zinc, and cobalt. Nickel is often used for ordinary purposes, and cobalt is used when it is desired to increase the degree of purification. Affinity purification using a polyhistidine-tag usually results in relatively pure protein when the recombinant protein is expressed in prokaryotic organisms. For example, prokaryotic or eukaryotic cells expressing a CD40-targeted polypeptide can be harvested via centrifugation and the resulting cell pellet lysed either by physical means (e.g., shearing, french-press, sonoication) or by means of detergents and enzymes such as lysozyme or any combination of these to produce a raw lysate containing the recombinant CD40-targeted protein among many other proteins originating from the host cell. This mixture is incubated with an affinity resin containing bound divalent nickel or cobalt ions, which are available commercially in different varieties. Nickel and cobalt have similar properties and as they are adjacent period 4 transition metals (v. iron triad). These resins are generally sepharose/agarose functionalised with a chelator, such as iminodiacetic acid (Ni-IDA) and nitrilotriacetic acid (Ni-NTA) for nickel and carboxylmethylaspartate (Co-CMA) for cobalt, which the polyhistidine-tag binds with micromolar affinity. The resin is then washed with phosphate buffer to remove proteins that do not specifically interact with the cobalt or nickel ion. With Ni-based methods, washing efficiency can be improved by the addition of 20 mM imidazole (proteins are usually eluted with 150-300 mM imidazole). Generally nickel-based resins have higher binding capacity, while cobalt-based resins offer the highest purity. The purity and amount of protein can be assessed by SDS-PAGE and Western blotting.

Other kinds of protein tags, such as those described by SEQ ID NOS: 13-17 may also be used to purify a fusion protein of the invention by binding to their corresponding substrates.

In some embodiments a polynucleotide sequence encoding a his-tag or other tag will be positioned after the start codon for the CD40-targeted polypeptide, in others, it may be positioned in the body of the polypeptide, for example, between residues derived from S1 and those derived from a CD40-binding ligand, and in others it may be positioned at the C-terminal of the polypeptide.

While tags are often incorporated at a C- or N-terminal of a protein a His tag of the invention as shown in the Example was placed the body of the fusion protein to facilitate recovery of the trimerized protein. The inventors found that this placement avoids cleavage of an N-terminally placed tag along with the signal peptide which usually occurs during protein secretion. Additionally, placing the tag in the body of the fusion protein can increase the flexibility of the fusion protein allowing it to more easily form a trimer.

In some embodiments, a polynucleotide sequence encoding a linker (e.g., gly-gly-gly or gly-ser-gly, or other linkers described herein) may be placed so as to encode an amino acid linker between residues derived from S1 protein or those derived from a CD40-binding ligand and the tag. Such a linker may be selected and positioned so as to prevent the tag from affecting the biological activity of the CD40-targeted polypeptide (e.g., recognition by the immune system or ability to bind to CD40) or to facilitate binding of the tag to its binding partner during affinity purification.

Any tag that can be captured by a binding molecule immobilized on a solid matrix can be used. For example, a poly-His-tag may be replaced by another affinity purification ligand such as a tag containing alternative histidine/glutamine or histidine/asparagine residues; e.g., tags comprising HQHQHQ (SEQ ID NO: 13) or HNHNHNHNHNHN (SEQ ID NO: 14) or a HAT tag such as KDHLIHNVHKEEHAHAHNK (SEQ ID NO: 15) which like poly-His tags also bind to metals described above via histidine. Other protein tags such as (strep)avidin, which binds to biotin, or Strep-tag II which is synthetic peptide consisting of eight amino acids, Trp-Ser-His-Pro-Gln-Phe-Glu-Lys (SEQ ID NO:17) which binds Strep-Tactin®, a specifically engineered streptavidin. Other protein tags and their corresponding binding ligands for affinity purification are known in the art and may be used instead of a His-tag. These include FLAG-tag, which comprises DYKDDDDK (SEQ ID NO: 16), chitin binding protein (CBP), maltose binding protein (MBP) and glutathione-S-transferase (GST).

In some embodiments, the tag will be removed during purification of the CD40-targeted polypeptide or after its trimerization, in others it may be left in the CD40-targeted polypeptide. In the embodiment exemplified herein, the His-tag is retained in the final vaccine fusion protein product, however, in other embodiments the fusion protein tag may be engineered to be removed from the final protein product.

The various segments of the CD40-targeted S1 fusion protein of the invention may appear in the order shown by FIG. 2 or 3 or in alternate orders that do not disrupt trimer formation or CD40 binding, for example, the CD40 ligand segment may appear toward the N-terminal of the fusion polypeptide and the S1 segment toward the C-terminal, or the tag may appear at the N- or C-terminal.

The polynucleotide and polypeptide sequences disclosed herein, such as those for MERS-CoV S1 protein, CD40 or CD40-like proteins, trimerization motifs, linkers, tags, and signal peptides, include those having sequence identity or similarity to the disclosed sequences, for example, that have between 70, 75, 80, 85, 90, 95, 96, 97, 98, 99, <100, or and 100% sequence identity or similarity to the disclosed polynucleotides or polypeptides. Typically, these variant proteins having substantial sequence identity or similarity will encode, or comprise, polypeptides that exhibit the same or similar properties as the disclosed sequence, for example, a variant S1 protein will exhibit similar immunological properties to a disclosed S1 sequence, a variant trimerization motif will facilitate trimerization, and a variant CD40-ligand will bind to CD40.

BLASTN may be used to identify a polynucleotide sequence having at least 70, 75, 80, 85, 90, 95, 96, 97, 98, 99, <100, or and 100% (or any intermediate %) sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are described by and incorporated by reference to to hypertext transfer protocol secure:// blast.ncbi.nlm.nih.gov/Blast.cgi?PROGRAM=blastn& BLAST_PROGRAMS=megaBlast&PAGE_TYPE= BlastSearch&SHOW_DEFAULTS=on&LINK_LOC=bl asthome (last accessed Aug. 7, 2018).

BLASTP can be used to identify an amino acid sequence having at least 70%, 75%, 80%, 85%, 87.5%, 90%, 92.5%, 95%, 96, 97.5% 98%, 99%, <100% or 100% (or any intermediate %) sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to to hypertext transfer protocol secure://blast.ncbi.nlm.nih.gov/Blast.cgi?PROGRAM= blastp&PAGE_TYPE=BlastSearch&LINK_LOC=blast-home (last accessed Aug. 7, 2018).

Vaccine platforms. A number of different vaccine platforms can be used to expose a subject's immune system to the CD40-targeted MERS-CoV S protein vaccine of the invention. These include a subunit vaccine from a purified trimeric fusion protein disclosed herein or from an immunogenically active fragment of the trimer; a DNA or RNA subunit vaccine prepared from DNA or RNA, or modified DNA or RNA, encoding the fusion protein, for example, for intramuscular injection of a plasmid or construct carrying a DNA or RNA subunit vaccine that encodes a fusion protein according to the invention that when injected expresses the fusion protein in the vaccinated subject; or a killed, nonreplicating, attenuated or living viral vaccine that carries a CD40-targeted fusion protein according to the invention or carries DNA or RNA encoding a CD40-targeted fusion protein, A virus-based vaccine may use one of many available virus platforms including an adenovirus 5 platform or rAD5 vector; see e.g. Amalfitano A, Hauser M A, Hu H, Serra D, Begy C R, Chamberlain J S. Production and characterization of improved adenovirus vectors with the E1, E2b, and E3 genes deleted. J Virol. 1998; 72:926-933; Gabitzsch, et al., Vaccine. 2009 Oct. 30; 27(46): 6394-6398 (both incorporated by reference). Other viral vectors that accommodate a chimeric gene that encodes CD40-targeted fusion protein according to the invention may also be selected.

In some embodiments a vaccine may be designed as a DIVA vaccine which (Differentiating Infected from Vaccinated Animals) which carry at least one epitope less than MERS-CoV strains circulating in the field. Such a vaccine facilitates later serological differentiation between infected and vaccinated animals by screening for the missing epitope, for example, with a monoclonal antibody that recognizes it in infected animals, but not in vaccinated, not infected animals.

A vaccine formulation, whether a protein-based vaccine, nucleic acid-based vaccine or virus-based vaccine may include additional ingredients such as excipients or adjuvants.

DNA-based vaccines. A chimeric nucleic acid in an acceptable liquid may be utilized as a direct immunizing agent, for example, as generally described by Felgner, et al., U.S. Pat. No. 5,589,466 or by Leitner, et al., Vaccine. 1999 Dec. 10; 18(9-10): 765-777, both of which are incorporated by reference. Vectors and procedures suitable for use in DNA vaccination are known and are also incorporated by reference to hypertext transfer protocol secure://en.wikipedia.org/wiki/DNA_vaccination (last accessed Oct. 3, 2018) and the articles cited therein.

Vaccine vectors include but are not limited to the Ad5 vector described by the inventors as well as vectors described by, and incorporated by reference to Choi, et al., Clin Exp Vaccine Res. 2013 July; 2(2): 97-105. These include adenovirus, alphavirus and pox virus vectors. Those skilled in the art may incorporate nucleic acids encoding the chimeric polypeptides of the invention into such vectors and administer such vectors according to current medical protocols.

Excipients. Typically, vaccines and/or immunogenic compositions of the invention will contain a pharmaceutically acceptable carrier or diluent. Carriers include, but are not limited to, stabilizers, preservatives, and buffers. Suitable stabilizers are, for example SPGA, polysorbate (Tween®) compositions, carbohydrates (such as sorbitol, mannitol, starch, sucrose, dextran, glutamate, or glucose), or proteins (such as albumin). Suitable preservatives include thimerosal, merthiolate, and gentamicin. Diluents include water and other aqueous buffers (such as normal or buffered saline), alcohols, and polyols such as glycerol. Vaccines and/or immunogenic compositions according to the various embodiments disclosed herein can be prepared, stored or distributed in solid, semisolid, liquid or aerosol form, for example, as a lyophilizate, a frozen solution, emulsion or suspension, a liquid solution, suspension or emulsion, or in a aerosol form.

Adjuvants. In some formulations of the vaccines and/or immunogenic compositions, suitable excipients, stabilizers, and the like may be added as are known by persons of ordinary skill in the art. In other embodiments, the immunogenic compositions further include or are administered with an adjuvant, such as an aluminum salt (e.g., aluminum hydroxide, aluminum phosphate, and aluminum potassium sulfate) or monophosphoryl lipid A which have been safely used in U.S. vaccines. In other formulations, no adjuvant will be incorporated with a CD40-targeted polypeptide of the invention.

Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 (an oil-in-water emulsion adjuvant); Montanide ISA 51 or 720 (a mineral oil-based or metabolizable oil-based adjuvant); aluminum hydroxide, -phosphate, or -oxide; HAVLOGEN®. (an acrylic acid polymer-based adjuvant, Intervet Inc., Millsboro, Del.); polyacrylic acids; oil-in-water or water-in-oil emulsion based on, for example a mineral oil, such as BAYOL or MARCOL™. (Esso Imperial Oil Limited, Canada), or a vegetable oil such as vitamin E acetate; and saponins. Components with adjuvant activity are widely known and, generally, any adjuvant may be utilized that does not adversely interfere with the efficacy or safety of the vaccine and/or immunogenic composition.

Method of inducing immunity. The invention contemplates a method for inducing an immune response in a subject or vaccinating a subject. This immune response includes at least one of a cellular or humoral response, or both, to MERS-CoV induced by the disclosed CD40-targeted fusion proteins. As shown by the inventor, the immune responses induced by a CD40-targeted S1 polypeptide are qualitatively different than those induced by a non-targeted S1 polypeptide in that the non-targeted S1 polypeptide induces vaccine-associated side-effects as shown by FIGS. 8A-8F.

The immunogenic CD40-targeted polypeptide or DNA encoding it can be formulated in accordance with standard techniques well known to those skilled in the pharmaceutical art and can be administered in dosages and by techniques well known to those skilled in the medical arts taking into consideration such factors as the age, sex, weight, respiratory status, and condition of the particular subject, and the route of administration.

The immunogenic CD40-targeted polypeptide or DNA/RNA encoding is typically administered intradermally, subcutaneously, submucosally, intranasally, intrapulmonarily, intramuscularly or by other parenteral route. Some other modes of administration include oral, administration on to or through a mucous membrane, such as to ocular tissue, sinus tissue, bronchial tissue, pulmonary tissue, enteric tissue, vaginal tissue, or rectal tissue.

An effective amount of the immunogenic CD40-targeted polypeptide or DNA/RNA encoding it is an amount that prevents or reduces the severity of or otherwise ameliorates MERS-CoV infection, reduces MERS-CoV titer, or alleviates the severity of symptoms of a MERS-CoV infection. Efficacy may be determined by comparing the level of protection in vitro or in vivo after immunization with that before immunization or by comparison to an unimmunized control group.

An immunogenic polypeptide or nucleic acid according to the invention may be administered prophylactically or therapeutically. In prophylactic administration, the vaccines can be administered in an amount sufficient to induce an immune response that protects against subsequent exposure to MERS-CoV, reduces the risk of being infected, or that reduces the severity of symptoms should a vaccinated subject become infected. Prophylactic administration of a vector, carrier or reservoir of MERS-CoV can reduce the risk of transmission to other susceptible subjects or eliminate or reduce viral titers in a carrier or reservoir of MERS-CoV. Prophylactic administration can also reduce the risk of transmission from food products, such as milk or meat, obtained from an animal that may be a MERS-CoV carrier or reservoir, for example, it may boost anti-MERS-CoV antibody titers in camelid milk, rendering it more safe for human consumption.

In therapeutic applications, the vaccines are administered to a subject in need thereof in an amount sufficient to elicit a therapeutic effect. An amount adequate to accomplish this is defined as a "therapeutically effective dose." Amounts effective for this use will depend on, e.g., the particular composition of the vaccine regimen administered, the manner of administration, the stage and severity of the disease, the general state of health of the patient, and the judgment of the prescribing physician. Preferably, an effective amount is selected that does not induce significant side-effects.

Vaccine administration. The vaccines and/or immunogenic compositions of the invention can be administered by immunization methods known to those of skill in the art. These include a single immunization or multiple immunizations in a prime-boost strategy. A boosting immunization can be administered at a time after the initial immunization that is days, weeks, months, or even years after the prime immunization. A boost immunization may be administered 0.5, 1, 2, 3, 4, 5, 6, 7, 8, 9, 10, 11, 12, 16, 20, or 24 months after the initial priming immunization.

In vitro or ex vivo immunization. In some embodiments, antigen presenting cells of a subject that express CD40 may be contacted with an immunogenic composition of the invention, then reinfused or otherwise returned to a subject. CD40 is constitutively expressed by antigen presenting cells, including dendritic cells, B cells and macrophages. For example, buffy coat cells may be isolated from the blood of a subject and contacted with a CD40-targeted S1 polypeptide of the invention for a time sufficient for binding of the CD40-targeted polypeptide to the antigen presenting cells, optionally washed to remove unbound polypeptide, and reinfused or otherwise returned to a subject. Alternatively bone marrow, cord blood cells, or isolated or cultured dendritic cells or other APCs may be used as a source of, or to produce, antigen presenting cells. As shown by the inventions, targeting an S1 polypeptide to antigen presenting cells using a ligand that binds to CD40 reduces vaccine-associated lung pathology compared to an untargeted S1 vaccine. In vitro or ex vivo immunization further reduces the non-targeted exposure of a subject to S1 epitopes and reduces the risk of immunological or inflammatory side-effects.

Subjects. The invention is typically directed to treatment of subjects susceptible to MERS CoV infection or subjects who are vectors, carriers, or reservoirs for this virus. Subjects include humans, as well as other primates, domestic animals, pets, such as camels or dromedaries, as well as wild animals which may act as reservoirs or vectors of the virus such as bats or birds. For non-human subjects a variant vaccine may be administered that contains a homolog of human CD40 ligand or a similar immune system protein.

DNA or RNA based vaccines. In some embodiments, DNA encoding a CD40-targeted S1 polypeptide of the invention may be replicated or synthesized by known methods. The DNA is then formulated for administration to a subject, for example, by intravenous, subcutaneous, intramuscular, intrapulmonary, or intralymphatic administration. DNA-based vaccines and methods of their use are known and are incorporated by reference to Tregoning, J S, et al., *Using Plasmids as DNA Vaccines for Infectious Diseases*. Microbiol Spectr. 2014 December; 2(6). doi: 10.1128/microbiolspec.PLAS-0028-2014; Ramirez, L A, et al., *Therapeutic and prophylactic DNA vaccines for HIV*-1. Expert Opin Biol Ther. 2013 April; 13(4):563-73. doi: 10.1517/14712598.2013.758709; Williams, J A, *Improving DNA vaccine performance through vector design*. Curr Gene Ther. 2014; 14(3):170-89. The above-cited references are each incorporated by reference.

In some embodiments, mRNA encoding a CD40-targeted S1 polypeptide of the invention may be produced by transcribing or otherwise producing an RNA molecule corresponding to DNA encoding the CD40-targeted polypeptide by known methods. The RNA is then formulated for administration to a subject, for example, by intravenous, subcutaneous, intramuscular, intrapulmonary, or intralymphatic administration. RNA-based vaccines and methods of using them to induce immunity are described by and incorporated by reference to Hubaud, A., RNA vaccines: a novel technology to prevent and treat disease, to hypertext transfer protocol secure://sitn.hms.harvard.edu/flash/2015/rna-vaccines-a-novel-technology-to-prevent-and-treat-disease/and to Pardi, N., et al., mRNA vaccines—a new era in vaccinology Nat Rev Drug Discov. 2018 April; 17(4):261-279. doi: 10.1038/nrd.2017.243. Epub 2018 Jan. 12.

Immune responses. Prophylactic or therapeutic immune responses induced by the polypeptide or nucleic acid based compositions of the invention can include humoral immune responses, such as activation of B cells and induction of IgA, IgG or IgM against MERS CoV, and cellular immune responses such as priming or expansion of T cells that recognize MERS CoV. Cellular immune responses are useful in protection against MERS-CoV virus infection with CD4+ and CD8+ T cell responses being important. CD8+ immunity is of importance in killing virally infected cells.

Other, non-limiting embodiments of the invention include those described below.

An engineered polypeptide that includes at least one immunogenic fragment, receptor-binding domain, or epitope of S1 polypeptide of Middle East respiratory syndrome coronavirus (MERS-CoV), at least one trimerization motif, and at least one ligand for CD40. This engineered CD40-targeted fusion polypeptide may include a native, consensus sequence from two or more isolates, or otherwise engineered MERS-CoV S1 protein sequence. MERS-CoV isolates include those from humans, camelids and other animals susceptible to infection by MERS-CoV or which act as carriers or reservoirs of MERS-CoV, and those described by the Centers for Disease Control at to hypertext transfer protocol secure://worldwideweb.nc.cdc.gov/eid/article/20/8/pdfs/14-0663.pdf (last accessed Aug. 22, 2018, incorporated by reference).

As shown in the Example, a fusion protein containing a MERS-CoV S1 consensus sequence was used to induce broad immune response by using conserved sequences which should cover any possible variation in viral sequences. All available MERS-CoV S sequences from GenBank database including isolates from all clades were used to design the consensus sequence. Such sequence may offer protection against broad range of MERS-CoV clades, including emerging strains.

This engineered polypeptide may contain an amino acid sequence that is at least 70, 75, 80, 85, 90, 95, 96, 97, 98, 99, <100 or 100% (or any intermediate value within this range) identical to the MERS CoV S1 consensus amino acid sequence of SEQ ID NO: 2 or is at least 70, 75, 80, 85, 90, 95, 96, 97, 98, 99, <100 or 100% (or any intermediate value within this range) identical to the engineered fusion polypeptide described by SEQ ID NO: 12. It may contain at 1, 2, 3, 4, 5, 6, 7, 8, 9, 10, 15, 20, 25, 30, 35, 40, 45, or 50 (or any intermediate integer value) amino acid residue deletions, substitutions or insertions to the amino acid sequences of SEQ ID NO: 2 or of SEQ ID NO: 12. In some embodiments, one or more conservative amino acid substitutions may be made to the amino acid sequences of SEQ ID NO: 2 or SEQ ID NO: 12 or to the signal peptide, S1, trimerization motif, or CD40 Ligand segments of the engineered polypeptide or to the linker or protein tag segments when present. The one or more conservative amino acid substitutions will be in the same class as the amino acid residue being substituted. Classes include aliphatic (glycine, alanine, valine, leucine, and isoleucine), hydroxyl- or sulfur/selenium-containing amino acids (serine, cysteine, selenocysteine, threonine, and methinone), cyclic (proline, hydroxyproline), aromatic (phenylalanine, tyrosine, tryptophan), basic (histidine, lysine, and arginine) and acid or acid-amides (aspartate, glutamate, asparagine and glutamine). The MERS-CoV S1 protein binds to the DPP4 (CD26) host cell receptor. Preferably, the S1 component of the engineered polypeptide contains amino acid residues involved in binding to this receptor.

A consensus sequence of S1 amino acid residues or other amino acid residues of the engineered polypeptide, such as CD40 ligand residues, may be constructed based on analysis of an alignment of multiple subtypes of a particular amino acid sequence, such as S1 amino acids of different kinds of MERS-CoV isolates. The consensus sequence may be used to induce broad immunity against multiple subtypes, serotypes, or strains of a particular viral antigen, such as the S1 subunit of MERS-CoV. In some embodiments, the polypeptide may include an S1 consensus sequence derived from the sequences of 2, 3, 4, 5, 6, 7, 8, 9, 10 or more different MERS-CoV S1 amino acid sequences. A MERS-CoV consensus sequence may be derived from the most virulent and/or most prevalent MERS-CoV strains in a geographical area at a particular time. Tools for deriving consensus sequences are well known in the art and include JalView and UGENE; see Waterhouse, A. M., Procter, J. B., Martin, D. M. A, Clamp, M. and Barton, G. J. (2009) *Jalview Version 2—a multiple sequence alignment editor and analysis workbench, Bioinformatics* 25 (9) 1189-1191 doi: 10.1093/bioinformatics/btp033; Okonechnikov K, Golosova O, Fursov M, the UGENE team. Unipro UGENE: a unified bioinformatics toolkit Bioinformatics 2012 28: 1166-1167. doi: 10.1093/bioinformatics/bts091 (both incorporated by reference).

An alternative to producing a MERS-CoV consensus sequence is to produce separate engineered CD40-targeted fusion polypeptides that have S1 amino acid sequences from 2, 3, 4, 5, 6, 7, 8, 9, or 10 different MERS-CoV isolates and then combine the engineered fusion polypeptides into a multivalent MERS-CoV vaccine.

Another alternative is to produce a single engineered CD40-targeted fusion polypeptide containing S1 epitopes from different MERS-CoV isolates. For example, the S1 receptor binding domains (or epitopes thereof) of 2, 3, 4, 5, 6, 7, 8, 9, 10 or more MERS-CoV isolates may be combined into a hybrid S1 segment of an engineered polypeptide according to the invention to provide a multivalent response against different MERS-CoV isolates.

This engineered CD40-targeted fusion polypeptide may also include a native, consensus sequence from two or more CD40 ligands, or otherwise engineered CD40 ligand sequence, including fragments or variants of a native CD40 ligand sequence that bind to CD40. Human CD40L is described by SEQ ID NO: 23 and camelid CD40Ls by SEQ ID NO: 25 and 27, though naturally-occurring variants, such as transcript variants, which generally have at least 95-<100% sequence identity to these sequences is also included. Orthologs of the CD40Ls described herein from other species that are at least 70, 75, 80, 85, 90, 95, 96, 97, 98, 99, <100% identical or similar to the CD40L disclosed herein and that bind to CD40 are also included.

Typically the CD40 ligand will be selected to recognize and bind to the CD40 molecule on antigen presenting cells of a subject to be vaccinated, for example, human CD40 for human subjects and camelid CD40 for camelid subjects. Human CD40 is described by SEQ ID NO: 18 and camelid CD40 by SEQ ID NO: 20, though naturally-occurring variants, such as transcript variant, homologs, or paralogs, which generally have at least 95-<100% sequence identity to these sequences is also included. Variant CD40L amino acid sequences that bind to CD40 may be at least 70, 75, 80, 85, 90, 95, 96, 97, 98, 99, <100% identical or similar to the CD40L disclosed herein.

An engineered fusion CD40-targeted fusion polypeptide of the invention typically includes at least one trimerization motif which facilitates or enables trimerization of the polypeptide into a form similar to a native trimeric structure on the MERS-CoV surface. Trimerized forms of S1 present both linear and conformation epitopes to which the humoral and cellular immune system can response. One such trimerization motif is described by a foldon sequence derived from T4 phage fibritin described in SEQ ID NO: 6 though other trimerization sequences may be used. This sequence when incorporated into a polypeptide stabilizes formation of a triple helix by the component protein monomers.

An engineered CD40-targeted S1 fusion polypeptide of the invention may contain additional elements to facilitate its expression or purification. For example, it may contain a leader sequence that permits its export from a host cell that expresses it, a linker that enhances its immunological activity or ability to bind to CD40 on antigen presenting cells or which sterically positions its component amino acid sequences, or a protein tag that facilitates its purification.

A signal peptide may be incorporated that facilitates expression and trafficking of a polypeptide of the invention. One example of a signal peptide is the native signal peptide of the MERS-CoV S protein or a variant thereof, though other signal peptides suitable for use in particular host cells may be used instead, such as those described by Kober, L, et al. (2013), id or by vonHeijne, G., et al., (1985), id.

A linker typically contains from 1 to 20 amino acid residues and may be positioned between the various polypeptide sequences of the engineered fusion protein of the invention, for example, between the S1 segment and the CD40L segment or next to a trimerization sequence or next to a protein tag. One such linker is the non-polar amino acid linker described by SEQ ID NO: 8 and encoded by SEQ ID NO: 7, though other non-polar linkers may also be used, preferably alanine or other non-polar amino acid residues.

An engineered CD40-targeted S1 fusion protein of the invention may also incorporate a protein tag to facilitate its isolation and purification. One such tag is a hexa-His tag (SEQ ID NO: 4), though other protein tags used to purify proteins may also be incorporated, such as those described by SEQ ID NOS: 13-17. A protein tag may be placed at the N-terminus, the C-terminus or at another position within the body of the engineered fusion protein where it can bind to its complementary substrate during purification.

An engineered fusion CD40-targeted S1 fusion polypeptide of the invention may be expressed by a chimeric polynucleotide, preferably one in a vector or DNA construct that can be transformed or transfected into a host cell and then expressed by the host cell. Advantageously, the coding sequences of the chimeric polynucleotide, including those encoding S1 and the CD40 ligand, are codon-optimized to modulate or maximize expression in a particular host cell, such as in Vero E6 cells. Software suitable for optimizing codon usage is known and may be used to optimize codon usage in a chimeric polynucleotide encoding an engineered CD40-targeted MERS-CoV S1 fusion polypeptide, see Optimizer available at hypertext transfer protocol://genomes._urv.cat/OPTIMIZER/ (last accessed Aug. 24, 2018). Codon usage frequencies for various organisms are known and are also incorporated by reference to the Codon Usage Database at worldwideweb.kazusa.or.jp/codon/ (last accessed Aug. 24, 2018).

An engineered fusion CD40-targeted S1 fusion polypeptide of the invention may be incorporated into a composition, such as a pharmaceutical composition or vaccine composition suitable for administration to a subject or in a concentrated or preserved form for later use. Such a composition typically will contain a pharmaceutically acceptable carrier, excipient and/or adjuvant or storage ingredients.

The engineered fusion CD40-targeted S1 fusion polypeptide of the invention or a polynucleotide encoding it may be administered to a subject in need of prophylaxis or treatment for MERS-CoV infection. Such a method may induce protective immunity, may reduce the risk of becoming infection, or reduce the severity of MERS-CoV infection or its symptoms, for example, this method may reduce viral titers in a subject including those in blood, serum, plasma, saliva, lavage fluid, sputum or other respiratory system secretions or in other biological samples obtained from the subject. The prophylactic or therapeutic administration of a polypeptide of the invention may reduce mortality or morbidity of MERS-CoV infection as measured by a decrease of fever, rhinorrhea (nasal discharge), cough, malaise (lethargy), shortness of breath, vomiting, diarrhea, anorexia, sneezing or other symptoms of respiratory distress, compared to a not immunized subject or to a subject immunized with a MERS-CoV vaccine that does not target CD40. MERS-CoV presence in a sample may be detected serologically or by detecting its nucleic acids by assays known in the art, such as ELISA or RT-PCR and clinical symptoms evaluated by those of skill in the medical arts.

A subject to whom a prophylactic or therapeutic composition of the invention is administered is preferably human, for example, a male or female child less than reproductive age, a male or female of reproductive age, a pregnant female, or an adult. The subject may be one at risk of exposure to MERS-CoV such as one who works in proximity to infected humans or animals or who is exposed to animal products like milk or meat, animal fluids such as saliva or blood, or animal waste products such as urine or feces, from an animal at risk of, of that is, infected with MERS-CoV. Subjects with impaired respiratory systems including pneumonia, cystic fibrosis, tuberculosis, asthma, emphysema, bronchitis, smokers, lung cancer, pneumoconiosis, and chronic bronchitis and other forms of COPD, autoimmune diseases, or those at risk of immune dysfunction or immunodeficiency may also be selected as subjects. Subjects at risk of vaccine-induced lung pathology may also be selected as the invention does not induce the severe side-effects observed for a non-targeted S1 vaccine.

A subject to whom the fusion protein or chimeric polynucleotide of the invention may be administered also includes non-human animals such as members of the Camelidae family, such as a dromedary or a Bactrian camel or llamas, alpacas, vicunas, or guanacos. A subject may also be a pet (e.g., dog or cat), livestock (e.g., horse, cattle, goats, sheep, pigs) or wild animal (e.g., bats, mice, rats) susceptible to infection with MERS-CoV or which act as a vectors, carriers or reservoirs for the virus. The term subject includes both adult and juvenile and male and female subjects. Preferably, a vaccine for use with a particular species will use the CD40L for that species, for example, dromedary CD40L (SEQ ID NO: 25) would be used for a dromedary vaccine, while human CD40L (SEQ ID NO: 23) would be used in an engineered CD40-targeted S1 polypeptide vaccine for humans.

Another embodiment of the invention is directed to a chimeric polynucleotide encoding an engineered CD40-targeted S1 polypeptide or other fusion polypeptide as disclosed herein. This polynucleotide may be DNA or RNA. It may form a part of a vector or DNA construct which is linear or circular. Typically, the polynucleotide will include initiation and termination signals operably linked to regulatory elements, such as a promoter sequence or a polyadenylation signal and are expressible in a host cell. In some embodiments, a DNA construct will be a vector or shuttle vector such as plasmid than can replicate in a prokaryotic cell, such as in *E. coli* or *B. subtilis* or that can replicate in a eukaryotic cell such as a yeast, insect or mammalian cell. A shuttle vector may contain origins of replication for both prokaryotic and eukaryotic cells permitting replication of the vector in either kind of cell. A vector may also contain one or more expression control sequences, such as promoters including inducible promoters, enhancer sequences, or ribosome binding sites, or one or more detectable marker sequences, such as polynucleotides that encode antibiotic resistance or detectable enzymes A vector or DNA construct of the invention may be transformed into a selected host cell which expresses the polynucleotide of the invention to obtain a polypeptide containing the desired immunogens or epitopes, such as S1 protein determinants. One example of such a vector is non-replicating recombinant adenovirus-5 (rAd5).

Many mammalian protein expression systems are known and commercially available including those described at to hypertext transfer protocol secure://worldwideweb.thermofisher.com/us/en/home/life-science/protein-biology/protein-expression/mammalian-protein-expression.html (incorporated by reference, last accessed Aug. 24, 2018). Prokaryotic and eukaryotic host cells that may be used to express mammalian proteins, such as MERS-CoV S1 which is naturally expressed by mammalian cellular machinery, include prokaryotic cells of *Escherichia coli, Corynebacgeriaum, Pseudomonasfiuroescens*; and eukaryotic host cells such as *Sacharomyces cerevisiae, Pichia Pastoris*, filamentous fungi, baculovirus-infected insect cells, *leishmania*, and a variety of mammalian cells such as Vero E6, Chinese Hamster ovary (CHO) and Human embryonic kidney (HEK) cells. Thus, one skilled in the art may select an appropriate vector and host cell expression system for transformation with a polynucleotide of the invention that encodes a CD40-targeted S1 fusion protein.

One embodiment of the chimeric polynucleotide of the invention is a nucleic acid based vaccine and a pharmaceutically acceptable carrier, excipient or adjuvant. Immune responses against MERS-CoV may be induced by administering a DNA- or RNA-based vaccine containing a chimeric polynucleotide encoding a CD40-targeted S1 fusion protein or other CD40-targeted polypeptide. A DNA- or RNA-based vaccine may be administered subcutaneously, intramuscularly, intravenously, intrapulmonarily, or intralymphatically. In one mode, the vaccine may be e complexed to particles or beads that are administered to an individual, for example, using a vaccine gun.

Another aspect of the invention is directed to a method for reducing side effects of administering a vaccine to a subject, especially a subject at risk of or suffering from a respiratory system disease or defect in immunity. As shown herein, non-targeted vaccination of a subject with MERS-CoV S1 antigen produced harmful effects in the lungs upon rechallenge of the vaccinated subject with MERS-CoV. The vaccines of the invention which target S1 to antigen presenting cells bearing CD40 avoid these harmful effects. A reduction in side effects may be quantified by comparison of a CD40-targeted vaccine with an otherwise identical or similar non-targeted vaccine.

Another embodiment of the invention is a kit containing the CD40-targeted MERS-CoV polypeptide or nucleic acid encoding this polypeptide as disclosed herein. The kit can be used to protect or treat a subject at risk of infection or who is infected with MERS-CoV. The kit may contain packaging materials such as sterile containers enclosing the MERS-CoV peptide, the polypeptide encoding it, an adjuvant, or a pharmaceutically acceptable excipient or carrier, or mixtures thereof. It may contain devices for administering these materials to a subject, such as a syringe and needle, a device for administration to a mucous membrane, such as an atomizer or inhaler for administration via the respiratory system, or an electroporation device for administration of RNA or DNA via the skin. It may also contain instructions for use. Any medium capable of storing instructions and communicating them to an end user may be used including package inserts, such as written instructions, or electronic storage media (e.g., magnetic discs, tapes, cartridges), optical media (e.g., CD ROM), and the like. The instructions for use of the kit may also include an address of an internet site which provides instructions.

EXAMPLES

In silico design and codon-optimization of the immunogen and generation of rAd vaccines. As described in the following example, a fusion gene was designed and codon-optimized to express a secreted and CD40-targeted consensus S1 protein.

The S1 segment of this fusion protein was designed to express a consensus MERS-CoV S1 subunit derived from all published MERS-CoV S1 protein sequences.

All available MERS-CoV S sequences were downloaded from GenBank database and this data set was filtered by removing sequences containing ambiguous amino acid codes. The final dataset was multiply aligned using CLUSTALW and the Shannon entropy for each amino acid position were determined and the consensus sequence was then obtained for S1 subunit (amino acids 1-747, SEQ ID NO: 2). The signal peptide from MERS-CoV S protein was maintained at the N-terminus so that the fusion protein can be secreted from rAd5-infected cells. The coding region for the consensus MERS-CoV S1 subunit (coding region 1-2241) was then codon-optimized for mammalian expression (SEQ ID NO: 2). The synthetic fusion gene was synthesized by linking the coding region of MERS-CoV S1 to a polynucleotide (SEQ ID NO: 3) encoding a histidine tag sequence HITHHHH (SEQ ID NO: 4), followed by a coding region (SEQ ID NO: 5) for a 27 amino acid residue fragment from the bacteriophage T4 fibritin trimerization motif GYIPEAPRDGQAYVRKDGEWVLLSTFL (SEQ ID NO: 6) connected via a coding region (SEQ ID NO: 7) for a non-polar amino acid linker AAA (SEQ ID NO: 8 where the terminal Xaas are not present) and to a coding region (SEQ ID NO: 9) for the ectodomain of CD40L amino acid residues 117-260 (SEQ ID NO: 10).

Figure 3:
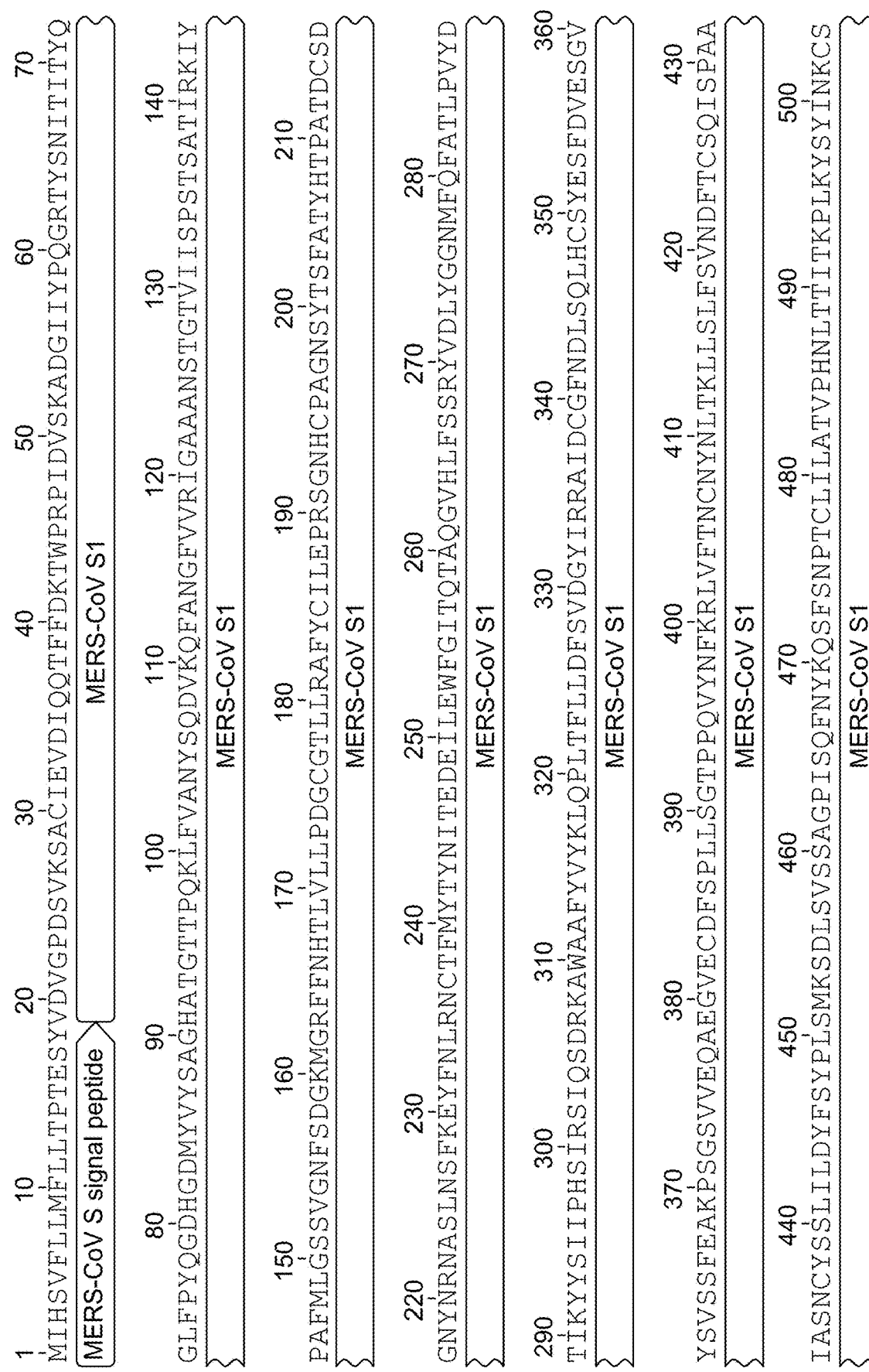
FIG. 3. The S1/F/CD40L fusion protein (SEQ ID NO: 11). Segments of the fusion protein from top to bottom: signal peptide, MERS-CoV S1, Histidine tag for affinity purification, bacteriophage T4 fibritin trimerization motif, nonpolar amino acid linker (AAA) and an ectodomain of CD40L.
Figure 3:
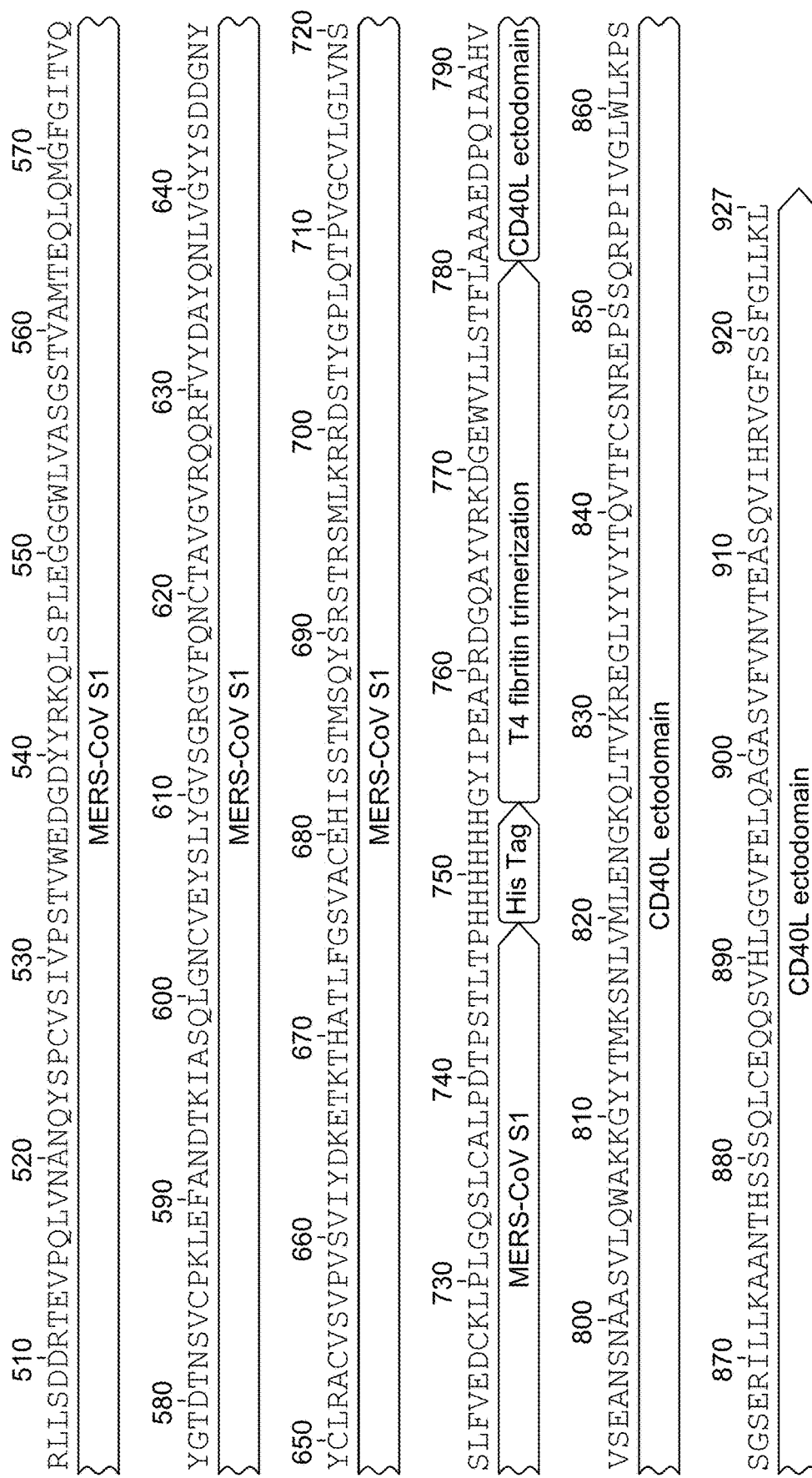
Figure 4:
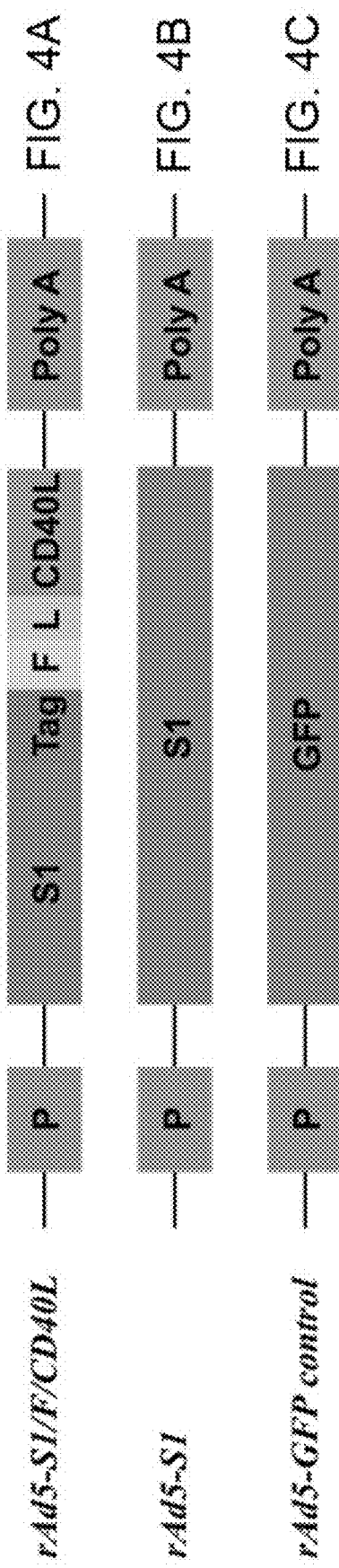
FIG. 4A. Schematic representation of DNA construct expressing CD40-targeted MERS-CoV vaccine rAd5-S1/F/CD40L which was engineered to express a fusion protein with the S1 subunit of the MERS-CoV S protein which contains the N-terminal S protein signal peptide, followed by a trimerization motif derived from T4 bacteriophage fibritin (F) fused with the ectodomain of mouse CD40 ligand at the C-terminus (CD40L). The S1 and CD40L are expressed within a trimerized fusion protein via F (S1/F/CD40L). The construct was placed under the control of a CMV promoter (CMV) and in front of BGH-poly A site (Poly A).
FIG. 4B. Schematic representation of a DNA construct expressing the non-CD40 targeted MERS-CoV vaccine construct rAd5-S1.
FIG. 4C. Schematic representation of a control DNA construct expressing GFP instead of MERS-CoV antigenic determinants.

This DNA construct (SEQ ID NO: 11) expresses the fusion protein S1/F/CD40L shown in FIG. 3 (SEQ ID NO: 12), which shows the whole coding region for the synthetic fusion gene. The fusion gene was then used to generate the proposed rAd construct, rAd5-S1/F/CD40L (FIG. 4A), in addition to rAd vaccines expressing secreted and consensus S1 protein alone (rAd5-S1)(FIG. 4B) and a vector control expressing GFP, rAd5-GFP (FIG. 4C), as shown in FIGS. 4A, 4B and 4C.

Cells and MERS-CoV virus. Vero E6 cells were cultured and maintained in complete Dulbecco's modified Eagle's medium (DMEM) supplemented with 10% heat-inactivated fetal bovine serum (FBS), and 100 U/ml penicillin and 100 µg/ml streptomycin in a humidified atmosphere of 5% $CO_2$ incubator. MERS-CoV-EMC/2012, was provided by Heinz Feldmann (NIH, NIAID Rocky Mountain Laboratories, Hamilton, Mont.) and Ron A. Fouchier (Erasmus Medical Center, Rotterdam, Netherlands). MERS-CoV amplification and culture was done in Vero E6 cells. The titer was determined by using $TCID_{50}$ assay and virus stocks were stored in aliquots at −80° C. All work involving infectious MERS-CoV was conducted within approved biosafety level 3 (BSL-3) at the National Galveston Laboratory.

Figure 5:
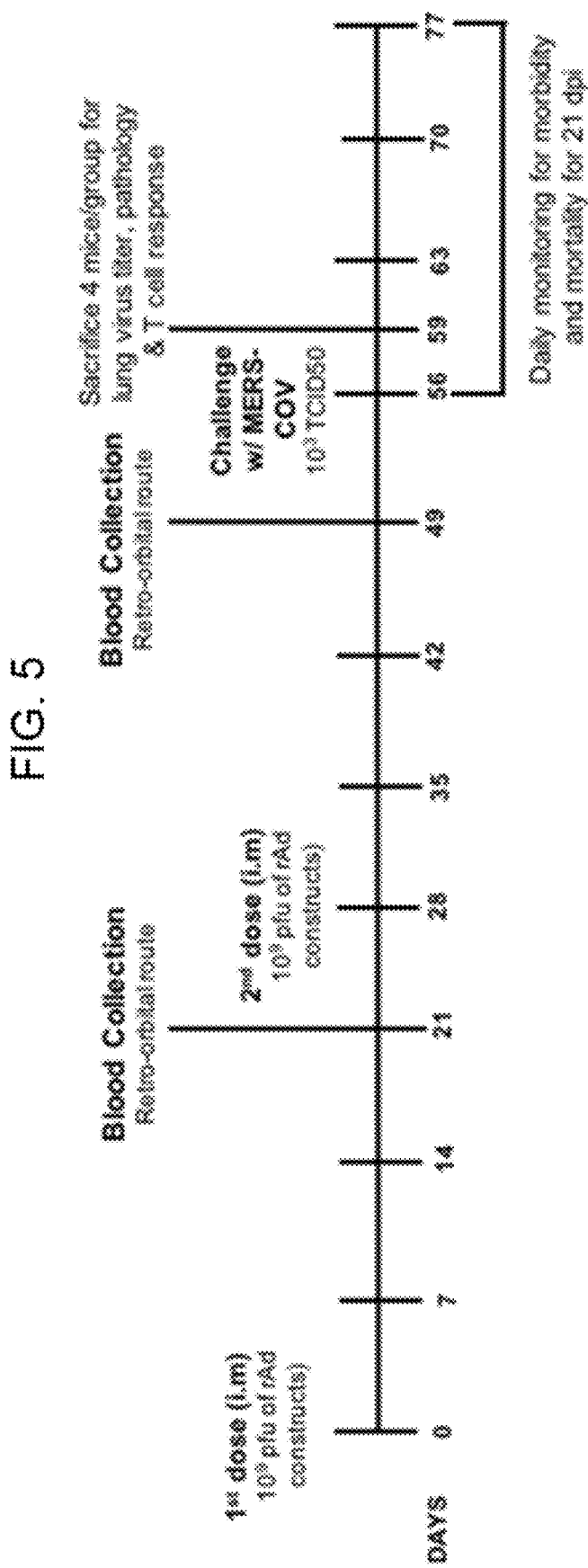
FIG. 5. Schematic representation of animal study design.

In vivo assessment. The immunogenicity and the protective efficacy of the developed rAd-based vaccines expressing the fusion protein rAd5-S1/F/CD40L, MERS-CoV subunit 1 (S1) of the spike protein rAd5-S1 or the control rAd vector rAd5-GFP were evaluated against MERS-CoV infection in a human DPP4 transgenic mouse model (hDPP4 Tg$^+$ mice). As shown in FIG. 5, a total of 45 hDPP4 Tg$^+$ mice aged 4-5 months were used in this study in which 15 mice were used per group. Mice were intramuscularly immunized twice, 28 days apart with 109 of rAd candidate vaccines. Blood samples were collected 3 weeks after each immunization to assess immunogenicity of the candidate vaccines by nAb assay. Five weeks post the second immunization, mice were intranasally (in) challenged with 103 (~100 $LD_{50}$) MERS-CoV (EMC2012 strain) and were monitored for morbidly (loss in body weight) and morbidity on daily bases. On day 3 post-infection, 4 mice from each group were sacrificed to assess the virus titer and pathology in their lungs. The remaining mice were monitored for morbidly and morbidity for up to 18 days. All animal experiments were performed in accordance with the Guide of NIH and AAALAC and were approved by the Institutional Animal Care and Use Committee at the University of Texas Medical Branch at Galveston, Tex., USA. Animals were housed in on-site animal facilities at Galveston National Laboratory under a 12:12 light/dark cycle with room temperature and humidity kept between 21-25° C. and 31-47%, respectively, with ad libitum access to food and water. All animal studies involving infectious MERS-CoV were conducted within approved animal BSL-3 laboratories at the National Galveston Laboratory, strictly following approved notification-of-usage (NOU) and animal protocols and the guidelines and regulations of the National Institutes of Health and AAALAC.

Lung pathology. At day 3 post challenge, 4 mice in each group were euthanized and their lungs were collected and examined for pathological changes after immunization and viral challenged. Briefly, lung tissues obtained from necropsy samples were fixed in 10% buffered formalin for 72 hrs, transferred to 70% ethanol, and later paraffin embedded. Histopathological evaluation was performed on deparaffinized sections stained by routine hematoxylin-eosin (H&E) staining. Evaluations for histopathology were done by pathologists at the department of pathology, UTBM, who were masked for each specimen source. Numeric scores were assigned to assess the extent of pathological damage.

Viral titration by $TCID_{50}$. Lungs collected from challenged mice on day 3 post-challenge were used to determine viral titer by $TCID_{50}$. Briefly, pieces of collected lung tissue specimens were weighed and homogenized in PBS containing 2% fetal calf serum (FCS) with a TissueLyser (Qiagen, Retsch, Haan, Germany). After clarification of the cellular and tissue debris by centrifugation, the titers of the resulting suspensions of infected tissues were determined using $TCID_{50}$ assay for quantifying yields of infectious virus. The virus titers of individual samples were expressed as log 10 $TCID_{50}$ per gram of tissue and the minimal detectable level of virus was 2.5 log 10 $TCID_{50}$ as determined by lung size.

Viral titration by RT-qPCR. Lung samples from each group of mice (n=4 per group) were transferred to individual vials containing RNA later solution and subsequently homogenized and subjected to total RNA isolation using TRIzol Reagent. To determine the viral titer in the lung, MERS-CoV-specific upstream E gene (upE) and endogenous control gene (mouse β-Actin) were quantified using one-step RT-PCR. Ct values for each sample were analyzed against Ct values generated from a standard curve of MERS-CoV mRNA copy number. Relative MERS-CoV upE mRNA expression value was calculated for each replicate and expressed as the equivalent of log 10 equivalents per gram (TCID eq/g) of the tissue by the standard threshold cycle (AACT) method using Bio-Rad CFX Manager 3.0 software.

Neutralizing Antibody Assays. The standard micro-neutralization assay was used to quantify the neutralizing Abs from immunized and control groups. Briefly, starting at a dilution of 1:10, 60-1 volumes of serial 2-fold dilutions of heat-inactivated serum specimens obtained 3 weeks after each immunization via retro-orbital bleeding were transferred into duplicate wells of 96-well plates containing 120 $TCID_{50}$ of MERS-CoV at 60 µl of DMEM medium/per well, giving a final volume of 120 µl/well. The antibody-virus mixtures were incubated at RT for 1 hr before transfer of 100 µl of the mixtures (containing 100 $TCID_{50}$ of MERS-CoV) into confluent Vero E6 cell monolayers in 96-well plates. Six wells of Vero E6 cells cultured with equal volumes of DMEM medium with and without virus were included in these assays as positive and negative controls, respectively. After 72 hrs of incubation, when the virus control wells exhibited advanced virus-induced CPE, the neutralizing capacity of individual serum samples was assessed by determining the presence or absence of CPE. Reciprocals of the last dilutions of serum specimens capable of completely preventing the formation of CPE in 50% of the wells were used as the neutralizing antibody titers and expressed as 50% neutralizing titers ($MNT_{50}$).

Data analysis. Statistical analysis was conducted using one-way ANOVA. Bonferroni's post-test was used to adjust for multiple comparisons between the different groups. All statistical analysis was conducted using GraphPad Prism software (San Diego, Calif.). P values <0.05 were considered significant.

A single dose of CD40-targeted MERS-CoV S1 elicited high levels of nAbs in mice. In order to evaluate the immunogenicity of our vaccine candidates, we immunized mice i.m. with two doses of the generated vaccines and measured the levels of nAbs before and 3 weeks after each immunization. All mice from all groups showed no detectable levels of nAbs in pre-bleed samples collected before immunization as expected. As shown in FIG. 6A, mice immunized with a single does of either rAd5-S1/F/CD40L or rAd-S1 elicited high levels of nAbs compared to control group (rAd-GFP), but only rAd5-S1/F/CD40L induced highly significant levels of nAbs against live MERS-CoV virus, suggesting that a single dose of rAd5-S1/F/CD40L could result in a strong humoral response and neutralizing activity when compared with rAd-S1. After boosting, all animals from both groups rAd5-S1/F/CD40L and rAd-S1 developed robust and significant levels of nAbs (FIG. 6B), indicating that at least two doses of rAd-S1 were required to induce levels of nAbs similar to those obtained by a single dose of rAd5-S1/F/CD40L. Furthermore, evaluation of circulating levels of S1-specific total IgG after one or two doses by ELISA also showed significantly higher levels in animals immunized with rAd5-S1/F/CD40L compared to rAd-S1 group (data not shown). These findings confirm that using CD40L as molecular adjuvant enhances the immunogenicity of S1 based vaccines and may represent a very promising vaccine platform to induce protective immunity with a single dose.

CD40-targeted MERS-CoV S1 protected mice from MERS-CoV without vaccine-associated lungpathology. To this end, immunized mice were challenged with 100 $LD_{50}$ of MERS-CoV in order to investigate the protective efficacy of the vaccines. Monitoring challenged animals for 3 weeks showed that both rAd5-S1 or rAd5-S1/F/CD40L immunized groups were completely protected (FIG. 7A) and maintained their weight (FIG. 7B), suggesting that both vaccines are protective in this highly MERS-CoV permissive mouse model and could represent potential vaccine candidates.

Evaluation of lung pathology in immunized and challenged mice on day 3 post-challenge showed that there was up to 15% of multiple monocytic and lymphocytic infiltrations in the lung of rAd5-GFP group compared to other groups which showed minimal or no lung infiltration (Table 1 and FIGS. 8A-8F).

TABLE 1

Viral titer and lung pathology.

| Vaccine | Animal | Viral titer ($\log_{10}$ $TCID_{50}$/g)[a] | Lung pathology (Grades 0-3)[d] |
|---|---|---|---|
| rAd5-empty | 1 | 4.16 | 1 |
| | 2 | 3.67 | 1 |
| | 3 | 3.51 | 1 |
| | 4 | 4.58 | 0 |
| | | 3.98 ± 0.24[b] | |
| rAd5-S1 | 1 | ND[c] | Hemorrhage |
| | 2 | ND | Hemorrhage |
| | 3 | ND | Hemorrhage |
| | 4 | ND | Hemorrhage |

TABLE 1-continued

Viral titer and lung pathology.

| Vaccine | Animal | Viral titer ($\log_{10}$ $TCID_{50}$/g)[a] | Lung pathology (Grades 0-3)[d] |
|---|---|---|---|
| rAd5-S1/F/CD40L | 1 | ND | 0 |
| | 2 | ND | 0 |
| | 3 | ND | 0 |
| | 4 | ND | 0-1[e] |

[a]rAd5-S1 and rAd5-S1/F/CD40L reduced MERS-CoV replication in the lungs of infected mice significantly (p = 0.015).
[b]= mean ± Sd.
[c]ND: not detected (below the detection limit of 2.5 $\log_{10}$).
[d]Grades 0-3: 0- normal/no pathology; 1-up to 15% pathology; 2-up to 25% pathology; 3-35% of the entire lung section with multiple monocytic and lymphocytic infiltrates.
[e]only small area with few infiltrates.

Surprisingly, while rAd5-S1 immunization protected animals from death and weight loss, and prevented lung infiltration similar to rAd5-S1/F/CD40L, the inventor observed perivascular hemorrhage in the whole lung of all examined mice (FIG. 8B, 8E). This is consistent with non-CD40-targeted S1 immunogen leading to vaccine-induced lung pathology, here, as characterized by pervascular hemorrhage.

On the other hand, immunization with rAd5-S1/F/CD40L protected mice to similar levels as rAd5-S1 but without such hemorrhage, indicating that using CD40L as targeting molecule and molecular adjuvant does not only enhance immunogenicity but also prevents vaccine-associated pulmonary pathology. Such vaccine-associated pathologies include interstitial lung disease, priming for a more serious enhanced MERS-CoV respiratory disease, hypersensitivity to MERS-CoV antigens, as well as other undesired inflammatory or immunological responses triggered or aggravated by vaccination and subsequent exposure to virus or viral antigens.

Figure 9:
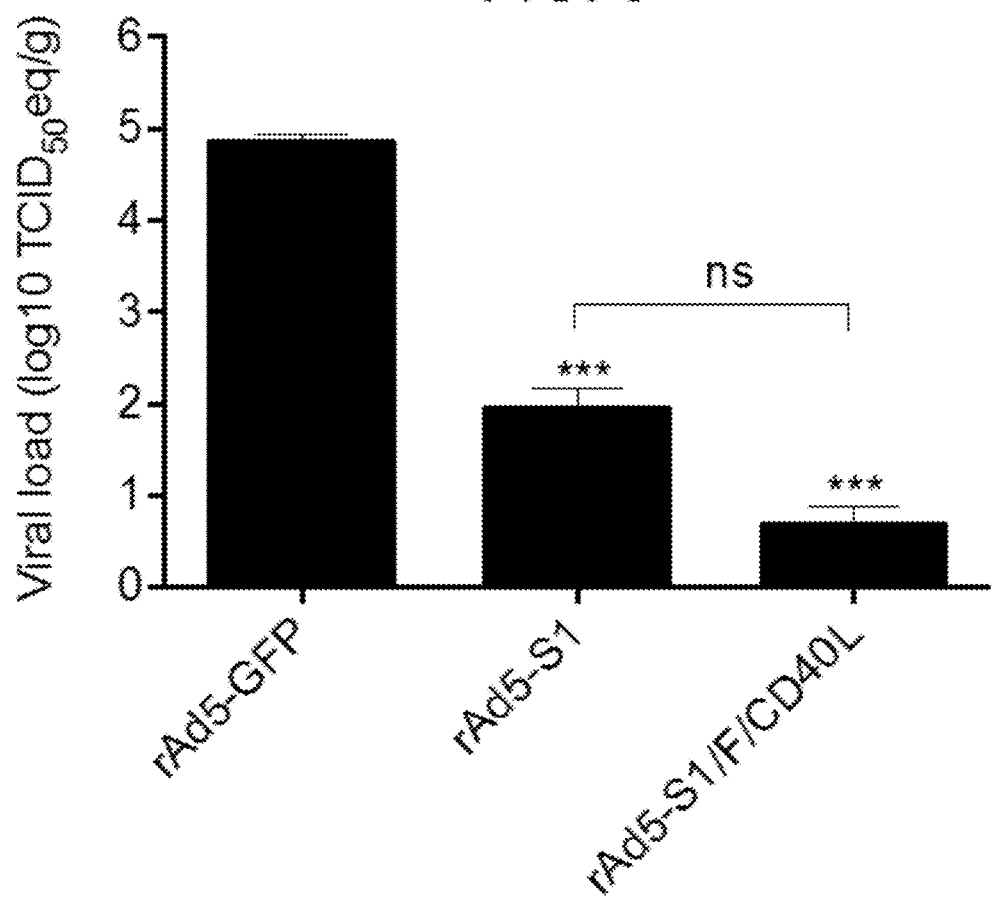
FIG. 9. Pulmonary viral load was determined in the lungs of immunized mice subsequently challenged with MERS-CoV. Viral load was determined as TCID50 equivalents (TCID eq/g) by qRT-PCR using a standard curve generated from dilutions of RNA from a MERS-CoV with known virus titer. Titers are shown as means from 4 mice per group±s.d from one experiment. ***P<0.001 (one-way ANOVA with Bonferroni's post-test). Highly significant reductions in viral titer compared to control (rAd5-GFP) were found for rAd5-S1 and rAd5-S1/F/CD40L.

Both MERS-CoV S1-based vaccines prevented pulmonary viral replication. To further confirm that the immunized mice were protected from MERS-CoV infection after challenge, we measured lung viral titer on day 3 post-challenge by $TCID_{50}$ and RT-qPCR. Analysis of lung viral titer by $TCID_{50}$ confirmed that both rAd5-S1/F/CD40L or rAd5-S1 vaccines prevented viral replication at a significant levels in the lungs of immunized mice compared to control animals to levels below the detection limits of $TCID_{50}$ assay (Table 1). Similarly, measurement of viral RNA in lungs demonstrated that both groups immunized with either rAd5-S1/F/CD40L or rAd5-S1 had significantly lower viral loads compared to the rAd-GFP control group by 3-4 logs as shown in FIG. 9. Although there was no significant difference between the viral load levels between rAd5-S1/F/CD40L and rAd5-S1, the viral load was lower by 1 log in rAd5-S1/F/CD40L immunized mice compared to rAd5-S1 group consistent with the overall stronger immune response we observed in this animal group.

The rapid spread and persistence of MERS-CoV in the Arabian Peninsula in addition to the associated high mortality rates represent a serious global public health concern especially that the elimination of the zoonotic reservoir is impossible. This threat is further complicated by the absence of prophylactic or therapeutic measures. Therefore, development of safe and preventive vaccine is urgently needed. Several groups have investigated various MERS-CoV vaccine platforms to combat MERS-CoV. See Wang et al.; Muthumani et al.; Coleman et al.; Du et al.; Al-Amri et al.; Ma et al.; Song et al.; Haagmans et al.; Guo et al.; Kim et al.; Alharbi et al.; and Agrawal et al., each incorporated herein by reference in their entirety. Most of these experimental vaccines were based on MERS-CoV full-length or truncated versions of the spike protein; these prototype vaccines induced high levels of nab and sometimes conferred complete protection against MERS-CoV challenge in several animal models. However, serious safety concerns are associated with vaccines for several CoVs including MERS-CoV and need to be elucidated and better understood. See Agrawal et al.; Weingartl et al.; Tseng et al.; Yang et al.; Czub et al.; Deming et al.; Olsen et al.; Jaume et al.; and Weiss et al; each incorporated herein by reference in their entirety.

As shown by the Example, both rAd expressing S1 or CD40-targeted S1 induced significant levels of anti-MERS-CoV systemic IgG and nAbs. However, the use of uCD40L as molecular adjuvant and targeting molecule enhanced the immunogenicity of S1 to the extent that one dose was sufficient to elicit significant levels of nAbs compared to control groups. Advantageously, both vaccines provided complete protection and prevented and/or minimized pulmonary viral replication and monocytic and lymphocytic lung infiltration in immunized mice compared to control group immunized with rAd5-GFP vector.

Surprisingly, it was found that mice immunized with the CD40L-targeted vaccine did not experience the severe perivascular hemorrhaging of the mice receiving the untargeted MERS-CoV S1 vaccine. As shown by FIG. 8, all examined mice receiving untargeted S1 (without CD40L) showed severe perivascular hemorrhage in the whole lung after viral challenge despite the observed robust immune response and protection. These results show that a CD40-targeted vaccine is safer than an otherwise similar S1 vaccine that is not targeted to CD40 on antigen presenting cells.

The inventor has shown that immunogens such as MERS-CoV S1 antigen may be targeted to CD40-expressing antigen presenting cells using a CD40L-type ligand and that such targeting enhances both immunogenicity and protective efficacy against virus challenge, but also minimizes the risk of side-effects such as respiratory pathology associated with the administration of non-targeted MERS-CoV vaccines. These results show the general applicability of this approach to production of vaccines to MERS-CoV as well as other kinds of viruses.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

---

The invention claimed is:

1. A vaccine composition for Middle East respiratory syndrome coronavirus (MERS-CoV), comprising:
   a polysorbate carrier,
   albumin,
   an aqueous buffer solution, and
   a polypeptide that comprises at least one receptor-binding domain, immunogenic fragment, or epitope of S1 polypeptide of MERS-CoV, at least one trimerization motif, and at least one ligand for CD40;
   wherein the at least one trimerization motif comprises the amino acid sequence of SEQ ID NO: 6; or
   wherein the CD40 ligand is human CD40L comprising the sequence of SEQ ID NO: 23 or a sequence that is at least 70% identical thereto, or a CD40-binding fragment thereof, or
   wherein the CD40 ligand is camelid or human CD40L comprising the sequence of SEQ ID NO: 25 or 27 or a sequence that is at least 70% identical thereto, or a CD40-binding fragment thereof.

2. The MERS-CoV vaccine of claim 1, wherein the at least one receptor-binding domain, immunogenic fragment, or epitope of S1 polypeptide of MERS-CoV comprises an amino acid sequence that is at least 70% identical to the amino acid sequence of SEQ ID NO: 2.

3. The MERS-CoV vaccine of claim 1, wherein the at least one receptor-binding domain, immunogenic fragment, or epitope of S1 polypeptide of MERS-CoV comprises a sequence of SEQ ID NO: 2.

4. The MERS-CoV vaccine of claim 1, wherein the at least one trimerization motif comprises the amino acid sequence of SEQ ID NO: 6.

5. The MERS-CoV vaccine of claim 1, wherein the CD40 ligand is human CD40L comprising the sequence of SEQ ID NO: 23 or a sequence that is at least 70% identical thereto, or a CD40-binding fragment thereof.

6. The MERS-CoV vaccine of claim 1, wherein the CD40 ligand is camelid or human CD40L comprising the sequence of SEQ ID NO: 25 or 27 or a sequence that is at least 70% identical thereto, or a CD40-binding fragment thereof.

7. The MERS-CoV vaccine of claim 1 that further comprises at least one peptide linker ranging from 1 to 10 amino acid residues in length between the at least one immunogenic fragment, receptor-binding domain, or epitope of S1 polypeptide of MERS-CoV, and/or the at least one trimerization motif, and/or the at least one ligand for CD40.

* * * * *

SEQUENCE LISTING

```
<160> NUMBER OF SEQ ID NOS: 27

<210> SEQ ID NO 1
<211> LENGTH: 2241
<212> TYPE: DNA
<213> ORGANISM: Artificial Sequence
<220> FEATURE:
<223> OTHER INFORMATION: Coding region for MERS-CoV consensus S1 subunit
<220> FEATURE:
<221> NAME/KEY: CDS
<222> LOCATION: (1)..(2241)

<400> SEQUENCE: 1 atg atc cac agc gtg ttc ctg ctg atg ttc ctg ctg acc ccc acc gag      48
Met Ile His Ser Val Phe Leu Leu Met Phe Leu Leu Thr Pro Thr Glu
1               5                   10                  15 agc tac gtg gac gtg ggc ccc gac agc gtg aag agc gcc tgc atc gag      96
Ser Tyr Val Asp Val Gly Pro Asp Ser Val Lys Ser Ala Cys Ile Glu
            20                  25                  30 gtg gac atc cag cag acc ttc ttc gac aag acc tgg ccc agg ccc atc     144
Val Asp Ile Gln Gln Thr Phe Phe Asp Lys Thr Trp Pro Arg Pro Ile
        35                  40                  45 gac gtg agc aag gcc gac ggc atc atc tac ccc cag ggc agg acc tac     192
Asp Val Ser Lys Ala Asp Gly Ile Ile Tyr Pro Gln Gly Arg Thr Tyr
    50                  55                  60 agc aac atc acc atc acc tac cag ggc ctg ttc ccc tac cag ggc gac     240
Ser Asn Ile Thr Ile Thr Tyr Gln Gly Leu Phe Pro Tyr Gln Gly Asp
65                  70                  75                  80
```

-continued

```
cac ggc gac atg tac gtg tac agc gcc ggc cac gcc acc ggc acc acc    288
His Gly Asp Met Tyr Val Tyr Ser Ala Gly His Ala Thr Gly Thr Thr
            85                  90                  95 ccc cag aag ctg ttc gtg gcc aac tac agc cag gac gtg aag cag ttc    336
Pro Gln Lys Leu Phe Val Ala Asn Tyr Ser Gln Asp Val Lys Gln Phe
        100                 105                 110 gcc aac ggc ttc gtg gtg agg atc ggc gcc gcc gcc aac agc acc ggc    384
Ala Asn Gly Phe Val Val Arg Ile Gly Ala Ala Ala Asn Ser Thr Gly
    115                 120                 125 acc gtg atc atc agc ccc agc acc agc gcc acc atc agg aag atc tac    432
Thr Val Ile Ile Ser Pro Ser Thr Ser Ala Thr Ile Arg Lys Ile Tyr
130                 135                 140 ccc gcc ttc atg ctg ggc agc agc gtg ggc aac ttc agc gac ggc aag    480
Pro Ala Phe Met Leu Gly Ser Ser Val Gly Asn Phe Ser Asp Gly Lys
145                 150                 155                 160 atg ggc agg ttc ttc aac cac acc ctg gtg ctg ctg ccc gac ggc tgc    528
Met Gly Arg Phe Phe Asn His Thr Leu Val Leu Leu Pro Asp Gly Cys
            165                 170                 175 ggc acc ctg ctg agg gcc ttc tac tgc atc ctg gag ccc agg agc ggc    576
Gly Thr Leu Leu Arg Ala Phe Tyr Cys Ile Leu Glu Pro Arg Ser Gly
        180                 185                 190 aac cac tgc ccc gcc ggc aac agc tac acc agc ttc gcc acc tac cac    624
Asn His Cys Pro Ala Gly Asn Ser Tyr Thr Ser Phe Ala Thr Tyr His
    195                 200                 205 acc ccc gcc acc gac tgc agc gac ggc aac tac aac agg aac gcc agc    672
Thr Pro Ala Thr Asp Cys Ser Asp Gly Asn Tyr Asn Arg Asn Ala Ser
210                 215                 220 ctg aac agc ttc aag gag tac ttc aac ctg agg aac tgc acc ttc atg    720
Leu Asn Ser Phe Lys Glu Tyr Phe Asn Leu Arg Asn Cys Thr Phe Met
225                 230                 235                 240 tac acc tac aac atc acc gag gac gag atc ctg gag tgg ttc ggc atc    768
Tyr Thr Tyr Asn Ile Thr Glu Asp Glu Ile Leu Glu Trp Phe Gly Ile
            245                 250                 255 acc cag acc gcc cag ggc gtg cac ctg ttc agc agc agg tac gtg gac    816
Thr Gln Thr Ala Gln Gly Val His Leu Phe Ser Ser Arg Tyr Val Asp
        260                 265                 270 ctg tac ggc ggc aac atg ttc cag ttc gcc acc ctg ccc gtg tac gac    864
Leu Tyr Gly Gly Asn Met Phe Gln Phe Ala Thr Leu Pro Val Tyr Asp
    275                 280                 285 acc atc aag tac tac agc atc atc ccc cac agc atc agg agc atc cag    912
Thr Ile Lys Tyr Tyr Ser Ile Ile Pro His Ser Ile Arg Ser Ile Gln
290                 295                 300 agc gac agg aag gcc tgg gcc gcc ttc tac gtg tac aag ctg cag ccc    960
Ser Asp Arg Lys Ala Trp Ala Ala Phe Tyr Val Tyr Lys Leu Gln Pro
305                 310                 315                 320 ctg acc ttc ctg ctg gac ttc agc gtg gac ggc tac atc agg agg gcc    1008
Leu Thr Phe Leu Leu Asp Phe Ser Val Asp Gly Tyr Ile Arg Arg Ala
            325                 330                 335 atc gac tgc ggc ttc aac gac ctg agc cag ctg cac tgc agc tac gag    1056
Ile Asp Cys Gly Phe Asn Asp Leu Ser Gln Leu His Cys Ser Tyr Glu
        340                 345                 350 agc ttc gac gtg gag agc ggc gtg tac agc gtg agc agc ttc gag gcc    1104
Ser Phe Asp Val Glu Ser Gly Val Tyr Ser Val Ser Ser Phe Glu Ala
    355                 360                 365 aag ccc agc ggc agc gtg gtg gag cag gcc gag ggc gtg gag tgc gac    1152
Lys Pro Ser Gly Ser Val Val Glu Gln Ala Glu Gly Val Glu Cys Asp
370                 375                 380 ttc agc ccc ctg ctg agc ggc acc ccc ccc cag gtg tac aac ttc aag    1200
Phe Ser Pro Leu Leu Ser Gly Thr Pro Pro Gln Val Tyr Asn Phe Lys
```

```
                385                 390                 395                 400
agg ctg gtg ttc acc aac tgc aac tac aac ctg acc aag ctg ctg agc          1248
Arg Leu Val Phe Thr Asn Cys Asn Tyr Asn Leu Thr Lys Leu Leu Ser
                    405                 410                 415 ctg ttc agc gtg aac gac ttc acc tgc agc cag atc agc ccc gcc gcc          1296
Leu Phe Ser Val Asn Asp Phe Thr Cys Ser Gln Ile Ser Pro Ala Ala
                    420                 425                 430 atc gcc agc aac tgc tac agc agc ctg atc ctg gac tac ttc agc tac          1344
Ile Ala Ser Asn Cys Tyr Ser Ser Leu Ile Leu Asp Tyr Phe Ser Tyr
                    435                 440                 445 ccc ctg agc atg aag agc gac ctg agc gtg agc agc gcc ggc ccc atc          1392
Pro Leu Ser Met Lys Ser Asp Leu Ser Val Ser Ser Ala Gly Pro Ile
                450                 455                 460 agc cag ttc aac tac aag cag agc ttc agc aac ccc acc tgc ctg atc          1440
Ser Gln Phe Asn Tyr Lys Gln Ser Phe Ser Asn Pro Thr Cys Leu Ile
465                 470                 475                 480 ctg gcc acc gtg ccc cac aac ctg acc acc atc acc aag ccc ctg aag          1488
Leu Ala Thr Val Pro His Asn Leu Thr Thr Ile Thr Lys Pro Leu Lys
                    485                 490                 495 tac agc tac atc aac aag tgc agc agg ctg ctg agc gac gac agg acc          1536
Tyr Ser Tyr Ile Asn Lys Cys Ser Arg Leu Leu Ser Asp Asp Arg Thr
                500                 505                 510 gag gtg ccc cag ctg gtg aac gcc aac cag tac agc ccc tgc gtg agc          1584
Glu Val Pro Gln Leu Val Asn Ala Asn Gln Tyr Ser Pro Cys Val Ser
                    515                 520                 525 atc gtg ccc agc acc gtg tgg gag gac ggc gac tac tac agg aag cag          1632
Ile Val Pro Ser Thr Val Trp Glu Asp Gly Asp Tyr Tyr Arg Lys Gln
                530                 535                 540 ctg agc ccc ctg gag ggc ggc ggc tgg ctg gtg gcc agc ggc agc acc          1680
Leu Ser Pro Leu Glu Gly Gly Gly Trp Leu Val Ala Ser Gly Ser Thr
545                 550                 555                 560 gtg gcc atg acc gag cag ctg cag atg ggc ttc ggc atc acc gtg cag          1728
Val Ala Met Thr Glu Gln Leu Gln Met Gly Phe Gly Ile Thr Val Gln
                    565                 570                 575 tac ggc acc gac acc aac agc gtg tgc ccc aag ctg gag ttc gcc aac          1776
Tyr Gly Thr Asp Thr Asn Ser Val Cys Pro Lys Leu Glu Phe Ala Asn
                580                 585                 590 gac acc aag atc gcc agc cag ctg ggc aac tgc gtg gag tac agc ctg          1824
Asp Thr Lys Ile Ala Ser Gln Leu Gly Asn Cys Val Glu Tyr Ser Leu
                    595                 600                 605 tac ggc gtg agc ggc agg ggc gtg ttc cag aac tgc acc gcc gtg ggc          1872
Tyr Gly Val Ser Gly Arg Gly Val Phe Gln Asn Cys Thr Ala Val Gly
                    610                 615                 620 gtg agg cag cag agg ttc gtg tac gac gcc tac cag aac ctg gtg ggc          1920
Val Arg Gln Gln Arg Phe Val Tyr Asp Ala Tyr Gln Asn Leu Val Gly
625                 630                 635                 640 tac tac agc gac gac ggc aac tac tac tgc ctg agg gcc tgc gtg agc          1968
Tyr Tyr Ser Asp Asp Gly Asn Tyr Tyr Cys Leu Arg Ala Cys Val Ser
                    645                 650                 655 gtg ccc gtg agc gtg atc tac gac aag gag acc aag acc cac gcc acc          2016
Val Pro Val Ser Val Ile Tyr Asp Lys Glu Thr Lys Thr His Ala Thr
                660                 665                 670 ctg ttc ggc agc gtg gcc tgc gag cac atc agc agc acc atg agc cag          2064
Leu Phe Gly Ser Val Ala Cys Glu His Ile Ser Ser Thr Met Ser Gln
                    675                 680                 685 tac agc agg agc acc agg agc atg ctg aag agg agg gac agc acc tac          2112
Tyr Ser Arg Ser Thr Arg Ser Met Leu Lys Arg Arg Asp Ser Thr Tyr
                690                 695                 700 ggc ccc ctg cag acc ccc gtg ggc tgc gtg ctg ggc ctg gtg aac agc          2160
Gly Pro Leu Gln Thr Pro Val Gly Cys Val Leu Gly Leu Val Asn Ser
```

```
Gly Pro Leu Gln Thr Pro Val Gly Cys Val Leu Gly Leu Val Asn Ser
705                 710                 715                 720 agc ctg ttc gtg gag gac tgc aag ctg ccc ctg ggc cag agc ctg tgc    2208
Ser Leu Phe Val Glu Asp Cys Lys Leu Pro Leu Gly Gln Ser Leu Cys
                725                 730                 735 gcc ctg ccc gac acc ccc agc acc ctg acc ccc                        2241
Ala Leu Pro Asp Thr Pro Ser Thr Leu Thr Pro
                740                 745
```

<210> SEQ ID NO 2
<211> LENGTH: 747
<212> TYPE: PRT
<213> ORGANISM: Artificial Sequence
<220> FEATURE:
<223> OTHER INFORMATION: Synthetic Construct

<400> SEQUENCE: 2

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
```

```
                305                 310                 315                 320
Leu Thr Phe Leu Leu Asp Phe Ser Val Asp Gly Tyr Ile Arg Arg Ala
                    325                 330                 335
Ile Asp Cys Gly Phe Asn Asp Leu Ser Gln Leu His Cys Ser Tyr Glu
                    340                 345                 350
Ser Phe Asp Val Glu Ser Gly Val Tyr Ser Val Ser Ser Phe Glu Ala
                    355                 360                 365
Lys Pro Ser Gly Ser Val Val Glu Gln Ala Glu Gly Val Glu Cys Asp
                    370                 375                 380
Phe Ser Pro Leu Leu Ser Gly Thr Pro Pro Gln Val Tyr Asn Phe Lys
385                 390                 395                 400
Arg Leu Val Phe Thr Asn Cys Asn Tyr Asn Leu Thr Lys Leu Leu Ser
                    405                 410                 415
Leu Phe Ser Val Asn Asp Phe Thr Cys Ser Gln Ile Ser Pro Ala Ala
                    420                 425                 430
Ile Ala Ser Asn Cys Tyr Ser Ser Leu Ile Leu Asp Tyr Phe Ser Tyr
                    435                 440                 445
Pro Leu Ser Met Lys Ser Asp Leu Ser Val Ser Ser Ala Gly Pro Ile
                    450                 455                 460
Ser Gln Phe Asn Tyr Lys Gln Ser Phe Ser Asn Pro Thr Cys Leu Ile
465                 470                 475                 480
Leu Ala Thr Val Pro His Asn Leu Thr Thr Ile Thr Lys Pro Leu Lys
                    485                 490                 495
Tyr Ser Tyr Ile Asn Lys Cys Ser Arg Leu Leu Ser Asp Asp Arg Thr
                    500                 505                 510
Glu Val Pro Gln Leu Val Asn Ala Asn Gln Tyr Ser Pro Cys Val Ser
                    515                 520                 525
Ile Val Pro Ser Thr Val Trp Glu Asp Gly Asp Tyr Tyr Arg Lys Gln
                    530                 535                 540
Leu Ser Pro Leu Glu Gly Gly Gly Trp Leu Val Ala Ser Gly Ser Thr
545                 550                 555                 560
Val Ala Met Thr Glu Gln Leu Gln Met Gly Phe Gly Ile Thr Val Gln
                    565                 570                 575
Tyr Gly Thr Asp Thr Asn Ser Val Cys Pro Lys Leu Glu Phe Ala Asn
                    580                 585                 590
Asp Thr Lys Ile Ala Ser Gln Leu Gly Asn Cys Val Glu Tyr Ser Leu
                    595                 600                 605
Tyr Gly Val Ser Gly Arg Gly Val Phe Gln Asn Cys Thr Ala Val Gly
                    610                 615                 620
Val Arg Gln Gln Arg Phe Val Tyr Asp Ala Tyr Gln Asn Leu Val Gly
625                 630                 635                 640
Tyr Tyr Ser Asp Asp Gly Asn Tyr Tyr Cys Leu Arg Ala Cys Val Ser
                    645                 650                 655
Val Pro Val Ser Val Ile Tyr Asp Lys Glu Thr Lys Thr His Ala Thr
                    660                 665                 670
Leu Phe Gly Ser Val Ala Cys Glu His Ile Ser Ser Thr Met Ser Gln
                    675                 680                 685
Tyr Ser Arg Ser Thr Arg Ser Met Leu Lys Arg Arg Asp Ser Thr Tyr
                    690                 695                 700
Gly Pro Leu Gln Thr Pro Val Gly Cys Val Leu Gly Leu Val Asn Ser
705                 710                 715                 720
Ser Leu Phe Val Glu Asp Cys Lys Leu Pro Leu Gly Gln Ser Leu Cys
                    725                 730                 735
```

```
Ala Leu Pro Asp Thr Pro Ser Thr Leu Thr Pro
            740                 745

<210> SEQ ID NO 3
<211> LENGTH: 18
<212> TYPE: DNA
<213> ORGANISM: Artificial Sequence
<220> FEATURE:
<223> OTHER INFORMATION: His tag
<220> FEATURE:
<221> NAME/KEY: CDS
<222> LOCATION: (1)..(18)

<400> SEQUENCE: 3 cac cac cac cac cac cac                                              18
His His His His His His
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

His His His His His His
1               5

<210> SEQ ID NO 5
<211> LENGTH: 81
<212> TYPE: DNA
<213> ORGANISM: Artificial Sequence
<220> FEATURE:
<223> OTHER INFORMATION: Coding region for trimerization motif
<220> FEATURE:
<221> NAME/KEY: CDS
<222> LOCATION: (1)..(81)

<400> SEQUENCE: 5 ggc tac atc ccc gag gcc ccc agg gac ggc cag gcc tac gtg agg aag     48
Gly Tyr Ile Pro Glu Ala Pro Arg Asp Gly Gln Ala Tyr Val Arg Lys
1               5                   10                  15 gac ggc gag tgg gtg ctg ctg agc acc ttc ctg                         81
Asp Gly Glu Trp Val Leu Leu Ser Thr Phe Leu
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic Construct

<400> SEQUENCE: 6

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 7
<211> LENGTH: 15
<212> TYPE: DNA
<213> ORGANISM: Artificial Sequence
<220> FEATURE:
<223> OTHER INFORMATION: Coding region for non-polar amino acid linker
<220> FEATURE:
```

```
<221> NAME/KEY: misc_feature
<222> LOCATION: (1)..(15)
<223> OTHER INFORMATION: Nucleotides 1-3 and 12-15 may be A, C, G or T
      or may be absent
<220> FEATURE:
<221> NAME/KEY: CDS
<222> LOCATION: (1)..(15)
<223> OTHER INFORMATION: Nucleotides 1-3 and 12-15 can code for any
      amino acid or, when absent, no amino acid.

<400> SEQUENCE: 7 nnn gcc gcc gcc nnn                                                   15
Xaa Ala Ala Ala Xaa
1               5

<210> SEQ ID NO 8
<211> LENGTH: 5
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: The 'Xaa' at location 1 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (5)..(5)
<223> OTHER INFORMATION: The 'Xaa' at location 5 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 8

Xaa Ala Ala Ala Xaa
1               5

<210> SEQ ID NO 9
<211> LENGTH: 435
<212> TYPE: DNA
<213> ORGANISM: Mus musculus
<220> FEATURE:
<221> NAME/KEY: CDS
<222> LOCATION: (1)..(435)
<223> OTHER INFORMATION: Coding sequence for murine CD40L ectodomain
      residues 117-260.

<400> SEQUENCE: 9 gag gac ccc cag atc gcc gcc cac gtg gtg agc gag gcc aac agc aac        48
Glu Asp Pro Gln Ile Ala Ala His Val Val Ser Glu Ala Asn Ser Asn
1               5                   10                  15 gcc gcc agc gtg ctg cag tgg gcc aag aag ggc tac tac acc atg aag        96
Ala Ala Ser Val Leu Gln Trp Ala Lys Lys Gly Tyr Tyr Thr Met Lys
                20                  25                  30 agc aac ctg gtg atg ctg gag aac ggc aag cag ctg acc gtg aag agg       144
Ser Asn Leu Val Met Leu Glu Asn Gly Lys Gln Leu Thr Val Lys Arg
            35                  40                  45 gag ggc ctg tac tac gtg tac acc cag gtg acc ttc tgc agc aac agg       192
Glu Gly Leu Tyr Tyr Val Tyr Thr Gln Val Thr Phe Cys Ser Asn Arg
        50                  55                  60 gag ccc agc agc cag agg ccc ttc atc gtg ggc ctg tgg ctg aag ccc       240
Glu Pro Ser Ser Gln Arg Pro Phe Ile Val Gly Leu Trp Leu Lys Pro
65                  70                  75                  80 agc agc ggc agc gag agg atc ctg ctg aag gcc gcc aac acc cac agc       288
Ser Ser Gly Ser Glu Arg Ile Leu Leu Lys Ala Ala Asn Thr His Ser
                85                  90                  95 agc agc cag ctg tgc gag cag cag agc gtg cac ctg ggc ggc gtg ttc       336
```

```
Ser Ser Gln Leu Cys Glu Gln Gln Ser Val His Leu Gly Gly Val Phe
            100                 105                 110 gag ctg cag gcc ggc gcc agc gtg ttc gtg aac gtg acc gag gcc agc      384
Glu Leu Gln Ala Gly Ala Ser Val Phe Val Asn Val Thr Glu Ala Ser
        115                 120                 125 cag gtg atc cac agg gtg ggc ttc agc agc ttc ggc ctg ctg aag ctg      432
Gln Val Ile His Arg Val Gly Phe Ser Ser Phe Gly Leu Leu Lys Leu
    130                 135                 140 tga                                                                  435

<210> SEQ ID NO 10
<211> LENGTH: 144
<212> TYPE: PRT
<213> ORGANISM: Mus musculus

<400> SEQUENCE: 10

Glu Asp Pro Gln Ile Ala Ala His Val Val Ser Glu Ala Asn Ser Asn
1               5                   10                  15

Ala Ala Ser Val Leu Gln Trp Ala Lys Lys Gly Tyr Tyr Thr Met Lys
            20                  25                  30

Ser Asn Leu Val Met Leu Glu Asn Gly Lys Gln Leu Thr Val Lys Arg
        35                  40                  45

Glu Gly Leu Tyr Tyr Val Tyr Thr Gln Val Thr Phe Cys Ser Asn Arg
    50                  55                  60

Glu Pro Ser Ser Gln Arg Pro Phe Ile Val Gly Leu Trp Leu Lys Pro
65                  70                  75                  80

Ser Ser Gly Ser Glu Arg Ile Leu Leu Lys Ala Ala Asn Thr His Ser
                85                  90                  95

Ser Ser Gln Leu Cys Glu Gln Gln Ser Val His Leu Gly Gly Val Phe
            100                 105                 110

Glu Leu Gln Ala Gly Ala Ser Val Phe Val Asn Val Thr Glu Ala Ser
        115                 120                 125

Gln Val Ile His Arg Val Gly Phe Ser Ser Phe Gly Leu Leu Lys Leu
    130                 135                 140

<210> SEQ ID NO 11
<211> LENGTH: 2784
<212> TYPE: DNA
<213> ORGANISM: Artificial Sequence
<220> FEATURE:
<223> OTHER INFORMATION: Coding region for S1-CD40L fusion protein
<220> FEATURE:
<221> NAME/KEY: CDS
<222> LOCATION: (1)..(2784)

<400> SEQUENCE: 11 atg atc cac agc gtg ttc ctg ctg atg ttc ctg ctg acc ccc acc gag       48
Met Ile His Ser Val Phe Leu Leu Met Phe Leu Leu Thr Pro Thr Glu
1               5                   10                  15 agc tac gtg gac gtg ggc ccc gac agc gtg aag agc gcc tgc atc gag       96
Ser Tyr Val Asp Val Gly Pro Asp Ser Val Lys Ser Ala Cys Ile Glu
            20                  25                  30 gtg gac atc cag cag acc ttc ttc gac aag acc tgg ccc agg ccc atc      144
Val Asp Ile Gln Gln Thr Phe Phe Asp Lys Thr Trp Pro Arg Pro Ile
        35                  40                  45 gac gtg agc aag gcc gac ggc atc atc tac ccc cag ggc agg acc tac      192
Asp Val Ser Lys Ala Asp Gly Ile Ile Tyr Pro Gln Gly Arg Thr Tyr
    50                  55                  60 agc aac atc acc atc acc tac cag ggc ctg ttc ccc tac cag ggc gac      240
Ser Asn Ile Thr Ile Thr Tyr Gln Gly Leu Phe Pro Tyr Gln Gly Asp
```

```
                     65                  70                  75                  80
cac ggc gac atg tac gtg tac agc gcc ggc cac gcc acc ggc acc acc      288
His Gly Asp Met Tyr Val Tyr Ser Ala Gly His Ala Thr Gly Thr Thr
                 85                  90                  95 ccc cag aag ctg ttc gtg gcc aac tac agc cag gac gtg aag cag ttc      336
Pro Gln Lys Leu Phe Val Ala Asn Tyr Ser Gln Asp Val Lys Gln Phe
            100                 105                 110 gcc aac ggc ttc gtg gtg agg atc ggc gcc gcc gcc aac agc acc ggc      384
Ala Asn Gly Phe Val Val Arg Ile Gly Ala Ala Ala Asn Ser Thr Gly
        115                 120                 125 acc gtg atc atc agc ccc agc acc agc gcc acc atc agg aag atc tac      432
Thr Val Ile Ile Ser Pro Ser Thr Ser Ala Thr Ile Arg Lys Ile Tyr
    130                 135                 140 ccc gcc ttc atg ctg ggc agc agc gtg ggc aac ttc agc gac ggc aag      480
Pro Ala Phe Met Leu Gly Ser Ser Val Gly Asn Phe Ser Asp Gly Lys
145                 150                 155                 160 atg ggc agg ttc ttc aac cac acc ctg gtg ctg ctg ccc gac ggc tgc      528
Met Gly Arg Phe Phe Asn His Thr Leu Val Leu Leu Pro Asp Gly Cys
                165                 170                 175 ggc acc ctg ctg agg gcc ttc tac tgc atc ctg gag ccc agg agc ggc      576
Gly Thr Leu Leu Arg Ala Phe Tyr Cys Ile Leu Glu Pro Arg Ser Gly
            180                 185                 190 aac cac tgc ccc gcc ggc aac agc tac acc agc ttc gcc acc tac cac      624
Asn His Cys Pro Ala Gly Asn Ser Tyr Thr Ser Phe Ala Thr Tyr His
        195                 200                 205 acc ccc gcc acc gac tgc agc gac ggc aac tac aac agg aac gcc agc      672
Thr Pro Ala Thr Asp Cys Ser Asp Gly Asn Tyr Asn Arg Asn Ala Ser
    210                 215                 220 ctg aac agc ttc aag gag tac ttc aac ctg agg aac tgc acc ttc atg      720
Leu Asn Ser Phe Lys Glu Tyr Phe Asn Leu Arg Asn Cys Thr Phe Met
225                 230                 235                 240 tac acc tac aac atc acc gag gac gag atc ctg gag tgg ttc ggc atc      768
Tyr Thr Tyr Asn Ile Thr Glu Asp Glu Ile Leu Glu Trp Phe Gly Ile
                245                 250                 255 acc cag acc gcc cag ggc gtg cac ctg ttc agc agc agg tac gtg gac      816
Thr Gln Thr Ala Gln Gly Val His Leu Phe Ser Ser Arg Tyr Val Asp
            260                 265                 270 ctg tac ggc ggc aac atg ttc cag ttc gcc acc ctg ccc gtg tac gac      864
Leu Tyr Gly Gly Asn Met Phe Gln Phe Ala Thr Leu Pro Val Tyr Asp
        275                 280                 285 acc atc aag tac tac agc atc atc ccc cac agc atc agg agc atc cag      912
Thr Ile Lys Tyr Tyr Ser Ile Ile Pro His Ser Ile Arg Ser Ile Gln
    290                 295                 300 agc gac agg aag gcc tgg gcc gcc ttc tac gtg tac aag ctg cag ccc      960
Ser Asp Arg Lys Ala Trp Ala Ala Phe Tyr Val Tyr Lys Leu Gln Pro
305                 310                 315                 320 ctg acc ttc ctg ctg gac ttc agc gtg gac ggc tac atc agg agg gcc     1008
Leu Thr Phe Leu Leu Asp Phe Ser Val Asp Gly Tyr Ile Arg Arg Ala
                325                 330                 335 atc gac tgc ggc ttc aac gac ctg agc cag ctg cac tgc agc tac gag     1056
Ile Asp Cys Gly Phe Asn Asp Leu Ser Gln Leu His Cys Ser Tyr Glu
            340                 345                 350 agc ttc gac gtg gag agc ggc gtg tac agc gtg agc agc ttc gag gcc     1104
Ser Phe Asp Val Glu Ser Gly Val Tyr Ser Val Ser Ser Phe Glu Ala
        355                 360                 365 aag ccc agc ggc agc gtg gtg gag cag gcc gag ggc gtg gag tgc gac     1152
Lys Pro Ser Gly Ser Val Val Glu Gln Ala Glu Gly Val Glu Cys Asp
    370                 375                 380 ttc agc ccc ctg ctg agc ggc acc ccc ccc cag gtg tac aac ttc aag     1200
```

| | | |
|---|---|---|
| Phe Ser Pro Leu Leu Ser Gly Thr Pro Pro Gln Val Tyr Asn Phe Lys<br>385                                    390                              395                             400 | | |
| agg ctg gtg ttc acc aac tgc aac tac aac ctg acc aag ctg ctg agc<br>Arg Leu Val Phe Thr Asn Cys Asn Tyr Asn Leu Thr Lys Leu Leu Ser<br>                          405                               410                             415 | | 1248 |
| ctg ttc agc gtg aac gac ttc acc tgc agc cag atc agc ccc gcc gcc<br>Leu Phe Ser Val Asn Asp Phe Thr Cys Ser Gln Ile Ser Pro Ala Ala<br>                    420                               425                             430 | | 1296 |
| atc gcc agc aac tgc tac agc agc ctg atc ctg gac tac ttc agc tac<br>Ile Ala Ser Asn Cys Tyr Ser Ser Leu Ile Leu Asp Tyr Phe Ser Tyr<br>            435                             440                             445 | | 1344 |
| ccc ctg agc atg aag agc gac ctg agc gtg agc agc gcc ggc ccc atc<br>Pro Leu Ser Met Lys Ser Asp Leu Ser Val Ser Ser Ala Gly Pro Ile<br>    450                             455                             460 | | 1392 |
| agc cag ttc aac tac aag cag agc ttc agc aac ccc acc tgc ctg atc<br>Ser Gln Phe Asn Tyr Lys Gln Ser Phe Ser Asn Pro Thr Cys Leu Ile<br>465                                  470                             475                             480 | | 1440 |
| ctg gcc acc gtg ccc cac aac ctg acc acc atc acc aag ccc ctg aag<br>Leu Ala Thr Val Pro His Asn Leu Thr Thr Ile Thr Lys Pro Leu Lys<br>                        485                             490                             495 | | 1488 |
| tac agc tac atc aac aag tgc agc agg ctg ctg agc gac gac agg acc<br>Tyr Ser Tyr Ile Asn Lys Cys Ser Arg Leu Leu Ser Asp Asp Arg Thr<br>                500                             505                             510 | | 1536 |
| gag gtg ccc cag ctg gtg aac gcc aac cag tac agc ccc tgc gtg agc<br>Glu Val Pro Gln Leu Val Asn Ala Asn Gln Tyr Ser Pro Cys Val Ser<br>            515                             520                             525 | | 1584 |
| atc gtg ccc agc acc gtg tgg gag gac ggc gac tac tac agg aag cag<br>Ile Val Pro Ser Thr Val Trp Glu Asp Gly Asp Tyr Tyr Arg Lys Gln<br>    530                             535                             540 | | 1632 |
| ctg agc ccc ctg gag ggc ggc ggc tgg ctg gtg gcc agc ggc agc acc<br>Leu Ser Pro Leu Glu Gly Gly Gly Trp Leu Val Ala Ser Gly Ser Thr<br>545                                  550                             555                             560 | | 1680 |
| gtg gcc atg acc gag cag ctg cag atg ggc ttc ggc atc acc gtg cag<br>Val Ala Met Thr Glu Gln Leu Gln Met Gly Phe Gly Ile Thr Val Gln<br>                        565                             570                             575 | | 1728 |
| tac ggc acc gac acc aac agc gtg tgc ccc aag ctg gag ttc gcc aac<br>Tyr Gly Thr Asp Thr Asn Ser Val Cys Pro Lys Leu Glu Phe Ala Asn<br>                580                             585                             590 | | 1776 |
| gac acc aag atc gcc agc cag ctg ggc aac tgc gtg gag tac agc ctg<br>Asp Thr Lys Ile Ala Ser Gln Leu Gly Asn Cys Val Glu Tyr Ser Leu<br>            595                             600                             605 | | 1824 |
| tac ggc gtg agc ggc agg ggc gtg ttc cag aac tgc acc gcc gtg ggc<br>Tyr Gly Val Ser Gly Arg Gly Val Phe Gln Asn Cys Thr Ala Val Gly<br>    610                             615                             620 | | 1872 |
| gtg agg cag cag agg ttc gtg tac gac gcc tac cag aac ctg gtg ggc<br>Val Arg Gln Gln Arg Phe Val Tyr Asp Ala Tyr Gln Asn Leu Val Gly<br>625                                  630                             635                             640 | | 1920 |
| tac tac agc gac gac ggc aac tac tac tgc ctg agg gcc tgc gtg agc<br>Tyr Tyr Ser Asp Asp Gly Asn Tyr Tyr Cys Leu Arg Ala Cys Val Ser<br>                645                             650                             655 | | 1968 |
| gtg ccc gtg agc gtg atc tac gac aag gag acc aag acc cac gcc acc<br>Val Pro Val Ser Val Ile Tyr Asp Lys Glu Thr Lys Thr His Ala Thr<br>            660                             665                             670 | | 2016 |
| ctg ttc ggc agc gtg gcc tgc gag cac atc agc agc acc atg agc cag<br>Leu Phe Gly Ser Val Ala Cys Glu His Ile Ser Ser Thr Met Ser Gln<br>    675                             680                             685 | | 2064 |
| tac agc agg agc acc agg agc atg ctg aag agg agg gac agc acc tac<br>Tyr Ser Arg Ser Thr Arg Ser Met Leu Lys Arg Arg Asp Ser Thr Tyr<br>          690                             695                             700 | | 2112 |

```
ggc ccc ctg cag acc ccc gtg ggc tgc gtg ctg ggc ctg gtg aac agc    2160
Gly Pro Leu Gln Thr Pro Val Gly Cys Val Leu Gly Leu Val Asn Ser
705                 710                 715                 720 agc ctg ttc gtg gag gac tgc aag ctg ccc ctg ggc cag agc ctg tgc    2208
Ser Leu Phe Val Glu Asp Cys Lys Leu Pro Leu Gly Gln Ser Leu Cys
                725                 730                 735 gcc ctg ccc gac acc ccc agc acc ctg acc ccc cac cac cac cac cac    2256
Ala Leu Pro Asp Thr Pro Ser Thr Leu Thr Pro His His His His His
            740                 745                 750 cac ggc tac atc ccc gag gcc ccc agg gac ggc cag gcc tac gtg agg    2304
His Gly Tyr Ile Pro Glu Ala Pro Arg Asp Gly Gln Ala Tyr Val Arg
        755                 760                 765 aag gac ggc gag tgg gtg ctg ctg agc acc ttc ctg gcc gcc gcc gag    2352
Lys Asp Gly Glu Trp Val Leu Leu Ser Thr Phe Leu Ala Ala Ala Glu
    770                 775                 780 gac ccc cag atc gcc gcc cac gtg gtg agc gag gcc aac agc aac gcc    2400
Asp Pro Gln Ile Ala Ala His Val Val Ser Glu Ala Asn Ser Asn Ala
785                 790                 795                 800 gcc agc gtg ctg cag tgg gcc aag aag ggc tac tac acc atg aag agc    2448
Ala Ser Val Leu Gln Trp Ala Lys Lys Gly Tyr Tyr Thr Met Lys Ser
                805                 810                 815 aac ctg gtg atg ctg gag aac ggc aag cag ctg acc gtg aag agg gag    2496
Asn Leu Val Met Leu Glu Asn Gly Lys Gln Leu Thr Val Lys Arg Glu
            820                 825                 830 ggc ctg tac tac gtg tac acc cag gtg acc ttc tgc agc aac agg gag    2544
Gly Leu Tyr Tyr Val Tyr Thr Gln Val Thr Phe Cys Ser Asn Arg Glu
        835                 840                 845 ccc agc agc cag agg ccc ttc atc gtg ggc ctg tgg ctg aag ccc agc    2592
Pro Ser Ser Gln Arg Pro Phe Ile Val Gly Leu Trp Leu Lys Pro Ser
    850                 855                 860 agc ggc agc gag agg atc ctg ctg aag gcc gcc aac acc cac agc agc    2640
Ser Gly Ser Glu Arg Ile Leu Leu Lys Ala Ala Asn Thr His Ser Ser
865                 870                 875                 880 agc cag ctg tgc gag cag cag agc gtg cac ctg ggc ggc gtg ttc gag    2688
Ser Gln Leu Cys Glu Gln Gln Ser Val His Leu Gly Gly Val Phe Glu
                885                 890                 895 ctg cag gcc ggc gcc agc gtg ttc gtg aac gtg acc gag gcc agc cag    2736
Leu Gln Ala Gly Ala Ser Val Phe Val Asn Val Thr Glu Ala Ser Gln
            900                 905                 910 gtg atc cac agg gtg ggc ttc agc agc ttc ggc ctg ctg aag ctg tga    2784
Val Ile His Arg Val Gly Phe Ser Ser Phe Gly Leu Leu Lys Leu
        915                 920                 925

<210> SEQ ID NO 12
<211> LENGTH: 927
<212> TYPE: PRT
<213> ORGANISM: Artificial Sequence
<220> FEATURE:
<223> OTHER INFORMATION: Synthetic Construct

<400> SEQUENCE: 12

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
```

-continued

```
             65                  70                  75                  80
His Gly Asp Met Tyr Val Tyr Ser Ala Gly His Ala Thr Gly Thr Thr
                     85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
                115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
                    180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495
```

```
Tyr Ser Tyr Ile Asn Lys Cys Ser Arg Leu Ser Asp Asp Arg Thr
            500                 505             510

Glu Val Pro Gln Leu Val Asn Ala Asn Gln Tyr Ser Pro Cys Val Ser
        515                 520             525

Ile Val Pro Ser Thr Val Trp Glu Asp Gly Asp Tyr Tyr Arg Lys Gln
        530                 535             540

Leu Ser Pro Leu Glu Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
            690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro His His His His His
            740                 745                 750

His Gly Tyr Ile Pro Glu Ala Pro Arg Asp Gly Gln Ala Tyr Val Arg
            755                 760                 765

Lys Asp Gly Glu Trp Val Leu Leu Ser Thr Phe Leu Ala Ala Ala Glu
            770                 775                 780

Asp Pro Gln Ile Ala Ala His Val Val Ser Glu Ala Asn Ser Asn Ala
785                 790                 795                 800

Ala Ser Val Leu Gln Trp Ala Lys Lys Gly Tyr Tyr Thr Met Lys Ser
                805                 810                 815

Asn Leu Val Met Leu Glu Asn Gly Lys Gln Leu Thr Val Lys Arg Glu
            820                 825                 830

Gly Leu Tyr Tyr Val Tyr Thr Gln Val Thr Phe Cys Ser Asn Arg Glu
            835                 840                 845

Pro Ser Ser Gln Arg Pro Phe Ile Val Gly Leu Trp Leu Lys Pro Ser
            850                 855                 860

Ser Gly Ser Glu Arg Ile Leu Leu Lys Ala Ala Asn Thr His Ser Ser
865                 870                 875                 880

Ser Gln Leu Cys Glu Gln Gln Ser Val His Leu Gly Gly Val Phe Glu
                885                 890                 895

Leu Gln Ala Gly Ala Ser Val Phe Val Asn Val Thr Glu Ala Ser Gln
            900                 905                 910
```

-continued

Val Ile His Arg Val Gly Phe Ser Ser Phe Gly Leu Leu Lys Leu
            915                 920                 925

<210> SEQ ID NO 13
<211> LENGTH: 6
<212> TYPE: PRT
<213> ORGANISM: Artificial Sequence
<220> FEATURE:
<223> OTHER INFORMATION: Protein tag

<400> SEQUENCE: 13

His Gln His Gln His Gln
1               5

<210> SEQ ID NO 14
<211> LENGTH: 12
<212> TYPE: PRT
<213> ORGANISM: Artificial Sequence
<220> FEATURE:
<223> OTHER INFORMATION: Protein tag

<400> SEQUENCE: 14

His Asn His Asn His Asn His Asn His Asn His Asn
1               5                   10

<210> SEQ ID NO 15
<211> LENGTH: 19
<212> TYPE: PRT
<213> ORGANISM: Artificial Sequence
<220> FEATURE:
<223> OTHER INFORMATION: Protein tag

<400> SEQUENCE: 15

Lys Asp His Leu Ile His Asn Val His Lys Glu Glu His Ala His Ala
1               5                   10                  15

His Asn Lys

<210> SEQ ID NO 16
<211> LENGTH: 8
<212> TYPE: PRT
<213> ORGANISM: Artificial Sequence
<220> FEATURE:
<223> OTHER INFORMATION: Protein tag

<400> SEQUENCE: 16

Asp Tyr Lys Asp Asp Asp Asp Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Strep-tag II

<400> SEQUENCE: 17

Trp Ser His Pro Gln Phe Glu Lys
1               5

<210> SEQ ID NO 18
<211> LENGTH: 1629
<212> TYPE: DNA
<213> ORGANISM: Homo sapiens
<220> FEATURE:
<221> NAME/KEY: misc_feature
<222> LOCATION: (1)..(1629)
<223> OTHER INFORMATION: Homo sapiens CD40 molecule (CD40), transcript variant 1, mRNA NCBI Reference Sequence: NM_001250.5
<220> FEATURE:
<221> NAME/KEY: sig_peptide
<222> LOCATION: (91)..(150)
<220> FEATURE:
<221> NAME/KEY: CDS
<222> LOCATION: (151)..(921)

<400> SEQUENCE: 18

```
tttcctgggc ggggccaagg ctggggcagg ggagtcagca gaggcctcgc tcgggcgccc      60
agtggtcctg ccgcctggtc tcacctcgct atggttcgtc tgcctctgca gtgcgtcctc     120
tggggctgct tgctgaccgc tgtccatcca gaa cca ccc act gca tgc aga gaa     174
                                  Glu Pro Pro Thr Ala Cys Arg Glu
                                   1               5 aaa cag tac cta ata aac agt cag tgc tgt tct ttg tgc cag cca gga     222
Lys Gln Tyr Leu Ile Asn Ser Gln Cys Cys Ser Leu Cys Gln Pro Gly
         10                  15                  20 cag aaa ctg gtg agt gac tgc aca gag ttc act gaa acg gaa tgc ctt     270
Gln Lys Leu Val Ser Asp Cys Thr Glu Phe Thr Glu Thr Glu Cys Leu
 25                  30                  35                  40 cct tgc ggt gaa agc gaa ttc cta gac acc tgg aac aga gag aca cac     318
Pro Cys Gly Glu Ser Glu Phe Leu Asp Thr Trp Asn Arg Glu Thr His
                 45                  50                  55 tgc cac cag cac aaa tac tgc gac ccc aac cta ggg ctt cgg gtc cag     366
Cys His Gln His Lys Tyr Cys Asp Pro Asn Leu Gly Leu Arg Val Gln
             60                  65                  70 cag aag ggc acc tca gaa aca gac acc atc tgc acc tgt gaa gaa ggc     414
Gln Lys Gly Thr Ser Glu Thr Asp Thr Ile Cys Thr Cys Glu Glu Gly
         75                  80                  85 tgg cac tgt acg agt gag gcc tgt gag agc tgt gtc ctg cac cgc tca     462
Trp His Cys Thr Ser Glu Ala Cys Glu Ser Cys Val Leu His Arg Ser
 90                  95                 100 tgc tcg ccc ggc ttt ggg gtc aag cag att gct aca ggg gtt tct gat     510
Cys Ser Pro Gly Phe Gly Val Lys Gln Ile Ala Thr Gly Val Ser Asp
105                 110                 115                 120 acc atc tgc gag ccc tgc cca gtc ggc ttc ttc tcc aat gtg tca tct     558
Thr Ile Cys Glu Pro Cys Pro Val Gly Phe Phe Ser Asn Val Ser Ser
                125                 130                 135 gct ttc gaa aaa tgt cac cct tgg aca agc tgt gag acc aaa gac ctg     606
Ala Phe Glu Lys Cys His Pro Trp Thr Ser Cys Glu Thr Lys Asp Leu
            140                 145                 150 gtt gtg caa cag gca ggc aca aac aag act gat gtt gtc tgt ggt ccc     654
Val Val Gln Gln Ala Gly Thr Asn Lys Thr Asp Val Val Cys Gly Pro
        155                 160                 165 cag gat cgg ctg aga gcc ctg gtg gtg atc ccc atc atc ttc ggg atc     702
Gln Asp Arg Leu Arg Ala Leu Val Val Ile Pro Ile Ile Phe Gly Ile
170                 175                 180 ctg ttt gcc atc ctc ttg gtg ctg gtc ttt atc aaa aag gtg gcc aag     750
Leu Phe Ala Ile Leu Leu Val Leu Val Phe Ile Lys Lys Val Ala Lys
185                 190                 195                 200 aag cca acc aat aag gcc ccc cac ccc aag cag gaa ccc cag gag atc     798
Lys Pro Thr Asn Lys Ala Pro His Pro Lys Gln Glu Pro Gln Glu Ile
                205                 210                 215 aat ttt ccc gac gat ctt cct ggc tcc aac act gct gct cca gtg cag     846
Asn Phe Pro Asp Asp Leu Pro Gly Ser Asn Thr Ala Ala Pro Val Gln
            220                 225                 230 gag act tta cat gga tgc caa ccg gtc acc cag gag gat ggc aaa gag     894
Glu Thr Leu His Gly Cys Gln Pro Val Thr Gln Glu Asp Gly Lys Glu
        235                 240                 245 agt cgc atc tca gtg cag gag aga cag tgaggctgca cccacccagg         941
Ser Arg Ile Ser Val Gln Glu Arg Gln
```

Ser Arg Ile Ser Val Gln Glu Arg Gln
            250                 255

```
agtgtggcca cgtgggcaaa caggcagttg gccagagagc ctggtgctgc tgctgctgtg   1001
gcgtgagggt gaggggctgg cactgactgg gcatagctcc ccgcttctgc ctgcacccct   1061
gcagtttgag acaggagacc tggcactgga tgcagaaaca gttcaccttg aagaacctct   1121
cacttcaccc tggagcccat ccagtctccc aacttgtatt aaagacagag cagaagtttt   1181
ggtggtggtg gtgttggggt atggtttagt aatatccacc agaccttccg atccagcagt   1241
ttggtgccca gagaggcatc atggtggctt ccctgcgccc aggaagccat atacacagat   1301
gcccattgca gcattgtttg tgatagtgaa caactggaag ctgcttaact gtccatcagc   1361
aggagactgg ctaaataaaa ttagaatata tttatacaac agaatctcaa aaacactgtt   1421
gagtaaggaa aaaaaggcat gctgctgaat gatgggtatg aacttttta aaaaagtaca    1481 tgctttatg tatgtatatt gcctatggat atatgtataa atacaatatg catcatatat    1541
tgatataaca agggttctgg aagggtacac agaaaaccca cagctcgaag agtggtgacg   1601
tctggggtgg ggaagaaggg tctgggggg                                     1629
```

<210> SEQ ID NO 19
<211> LENGTH: 257
<212> TYPE: PRT
<213> ORGANISM: Homo sapiens

<400> SEQUENCE: 19

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Ala Gly Thr Asn
145                 150                 155                 160

Lys Thr Asp Val Val Cys Gly Pro Gln Asp Arg Leu Arg Ala Leu Val
                165                 170                 175

Val Ile Pro Ile Ile Phe Gly Ile Leu Phe Ala Ile Leu Leu Val Leu
            180                 185                 190

Val Phe Ile Lys Lys Val Ala Lys Lys Pro Thr Asn Lys Ala Pro His
        195                 200                 205

Pro Lys Gln Glu Pro Gln Glu Ile Asn Phe Pro Asp Asp Leu Pro Gly
    210                 215                 220

Ser Asn Thr Ala Ala Pro Val Gln Glu Thr Leu His Gly Cys Gln Pro
225                 230                 235                 240

```
Val Thr Gln Glu Asp Gly Lys Glu Ser Arg Ile Ser Val Gln Glu Arg
            245                 250                 255

Gln

<210> SEQ ID NO 20
<211> LENGTH: 970
<212> TYPE: DNA
<213> ORGANISM: Camelus dromedarius
<220> FEATURE:
<221> NAME/KEY: CDS
<222> LOCATION: (69)..(902)
<223> OTHER INFORMATION: PREDICTED: Camelus dromedarius CD40 molecule,
      TNF receptor superfamily member 5 (CD40), transcript variant X1,
      mRNA NCBI Reference Sequence: XM_010978624.1

<400> SEQUENCE: 20
gggcagggga actggtagag gcccaggccc ggcgccctct gctcccaccg cctggtgctc       60 acctcgcc atg gtt cgc ctg cct ctg cag tgt ctc ctc tgg ggt tgc ttt      110
         Met Val Arg Leu Pro Leu Gln Cys Leu Leu Trp Gly Cys Phe
         1               5                   10 ttg acc acc gtc cac cca gaa cca ctc act gca tgc aga gaa gac caa      158
Leu Thr Thr Val His Pro Glu Pro Leu Thr Ala Cys Arg Glu Asp Gln
15              20                  25                  30 tat cta ata aac agt cag tgc tgt aat ctg tgc ccg cca gga gag aaa      206
Tyr Leu Ile Asn Ser Gln Cys Cys Asn Leu Cys Pro Pro Gly Glu Lys
                35                  40                  45 ctg gtg aac gac tgc aca gag gtc acc gcc aca gaa tgc ctt cct tgc      254
Leu Val Asn Asp Cys Thr Glu Val Thr Ala Thr Glu Cys Leu Pro Cys
            50                  55                  60 agt aac ggc gaa ttt ata gcc acc tgg aac aga gag aaa cac tgt cac      302
Ser Asn Gly Glu Phe Ile Ala Thr Trp Asn Arg Glu Lys His Cys His
        65                  70                  75 cag cac aaa tac tgt gac ccc aac cta ggg ctc ctg gtc cag agg gag      350
Gln His Lys Tyr Cys Asp Pro Asn Leu Gly Leu Leu Val Gln Arg Glu
    80                  85                  90 ggc act tcg aaa aca gac acc att tgc ata tgt gaa gaa gat caa cac      398
Gly Thr Ser Lys Thr Asp Thr Ile Cys Ile Cys Glu Glu Asp Gln His
95                  100                 105                 110 tgt acc agt gac acc tgc gaa agt tgc acc ctg aac agc ttg tgc ctc      446
Cys Thr Ser Asp Thr Cys Glu Ser Cys Thr Leu Asn Ser Leu Cys Leu
                115                 120                 125 cct ggc ctc ggg gtc aag cag atc gct aca ggg gtc tct gat acc atc      494
Pro Gly Leu Gly Val Lys Gln Ile Ala Thr Gly Val Ser Asp Thr Ile
            130                 135                 140 tgt gaa ccc tgc ccg gtt ggc ttc ttc tcc aac gtg tca tct gct ttt      542
Cys Glu Pro Cys Pro Val Gly Phe Phe Ser Asn Val Ser Ser Ala Phe
        145                 150                 155 gaa aag tgt tac cct tgg aca agc tgt gag agc aaa ggc ctc gtg gag      590
Glu Lys Cys Tyr Pro Trp Thr Ser Cys Glu Ser Lys Gly Leu Val Glu
    160                 165                 170 caa cgt gca ggg act aac aag act gat gtc atc tgt ggt ttc cag cat      638
Gln Arg Ala Gly Thr Asn Lys Thr Asp Val Ile Cys Gly Phe Gln His
175                 180                 185                 190 cgg atg aga gcc ctg gtg gtg atc ccc atc acg atg ggg atc ctg ttt      686
Arg Met Arg Ala Leu Val Val Ile Pro Ile Thr Met Gly Ile Leu Phe
                195                 200                 205 gct gtc ctg ttg gta tct gcc tgt atc agt gag tcc cca gga aag gtg      734
Ala Val Leu Leu Val Ser Ala Cys Ile Ser Glu Ser Pro Gly Lys Val
            210                 215                 220 gcc aag gag caa gag act aag atc ctc cac cct aag gct gaa agg cag      782
```

```
Ala Lys Glu Gln Glu Thr Lys Ile Leu His Pro Lys Ala Glu Arg Gln
            225                 230                 235 gat cct gtg gag acg att gat cct gac ccc act cca gtg caa gag acc      830
Asp Pro Val Glu Thr Ile Asp Pro Asp Pro Thr Pro Val Gln Glu Thr
        240                 245                 250 tta cac tgg tgc cag ccg gtc acc cag gag gat ggc aag gaa agc cgc      878
Leu His Trp Cys Gln Pro Val Thr Gln Glu Asp Gly Lys Glu Ser Arg
255                 260                 265                 270 atc tct gtg cag gag cga gag tga ggctgtgcgt gcccaggagc gtgcaacatg     932
Ile Ser Val Gln Glu Arg Glu
                275 ggcacgtggc cagagagcct ggggctgctg cagcggcg                            970
```

<210> SEQ ID NO 21
<211> LENGTH: 277
<212> TYPE: PRT
<213> ORGANISM: Camelus dromedarius

<400> SEQUENCE: 21

```
Met Val Arg Leu Pro Leu Gln Cys Leu Leu Trp Gly Cys Phe Leu Thr
1               5                   10                  15

Thr Val His Pro Glu Pro Leu Thr Ala Cys Arg Glu Asp Gln Tyr Leu
            20                  25                  30

Ile Asn Ser Gln Cys Cys Asn Leu Cys Pro Pro Gly Glu Lys Leu Val
        35                  40                  45

Asn Asp Cys Thr Glu Val Thr Ala Thr Glu Cys Leu Pro Cys Ser Asn
    50                  55                  60

Gly Glu Phe Ile Ala Thr Trp Asn Arg Glu Lys His Cys His Gln His
65                  70                  75                  80

Lys Tyr Cys Asp Pro Asn Leu Gly Leu Leu Val Gln Arg Glu Gly Thr
                85                  90                  95

Ser Lys Thr Asp Thr Ile Cys Ile Cys Glu Glu Asp Gln His Cys Thr
            100                 105                 110

Ser Asp Thr Cys Glu Ser Cys Thr Leu Asn Ser Leu Cys Leu Pro Gly
        115                 120                 125

Leu Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys Tyr Pro Trp Thr Ser Cys Glu Ser Lys Gly Leu Val Glu Gln Arg
                165                 170                 175

Ala Gly Thr Asn Lys Thr Asp Val Ile Cys Gly Phe His Arg Met
            180                 185                 190

Arg Ala Leu Val Val Ile Pro Ile Thr Met Gly Ile Leu Phe Ala Val
        195                 200                 205

Leu Leu Val Ser Ala Cys Ile Ser Glu Ser Pro Gly Lys Val Ala Lys
    210                 215                 220

Glu Gln Glu Thr Lys Ile Leu His Pro Lys Ala Glu Arg Gln Asp Pro
225                 230                 235                 240

Val Glu Thr Ile Asp Pro Asp Pro Thr Pro Val Gln Glu Thr Leu His
                245                 250                 255

Trp Cys Gln Pro Val Thr Gln Glu Asp Gly Lys Glu Ser Arg Ile Ser
            260                 265                 270

Val Gln Glu Arg Glu
        275
```

```
<210> SEQ ID NO 22
<211> LENGTH: 1859
<212> TYPE: DNA
<213> ORGANISM: Homo sapiens
<220> FEATURE:
<221> NAME/KEY: CDS
<222> LOCATION: (73)..(858)
<223> OTHER INFORMATION: Homo sapiens CD40 ligand, mRNA (cDNA clone
      MGC:88303 IMAGE:30418744), complete cds GenBank: BC071754.1

<400> SEQUENCE: 22
actttgacag tcttctcatg ctgcctctgc caccttctct gccagaagat accatttcaa        60
ctttaacaca gc atg atc gaa aca tac aac caa act tct ccc cga tct gcg      111
              Met Ile Glu Thr Tyr Asn Gln Thr Ser Pro Arg Ser Ala
                1               5                  10 gcc act gga ctg ccc atc agc atg aaa att ttt atg tat tta ctt act        159
Ala Thr Gly Leu Pro Ile Ser Met Lys Ile Phe Met Tyr Leu Leu Thr
 15                  20                  25 gtt ttt ctt atc acc cag atg att ggg tca gca ctt ttt gct gtg tat        207
Val Phe Leu Ile Thr Gln Met Ile Gly Ser Ala Leu Phe Ala Val Tyr
 30                  35                  40                  45 ctt cat aga agg ttg gac aag ata gaa gat gaa agg aat ctt cat gaa        255
Leu His Arg Arg Leu Asp Lys Ile Glu Asp Glu Arg Asn Leu His Glu
                 50                  55                  60 gat ttt gta ttc atg aaa acg ata cag aga tgc aac aca gga gaa aga        303
Asp Phe Val Phe Met Lys Thr Ile Gln Arg Cys Asn Thr Gly Glu Arg
             65                  70                  75 tcc tta tcc tta ctg aac tgt gag gag att aaa agc cag ttt gaa ggc        351
Ser Leu Ser Leu Leu Asn Cys Glu Glu Ile Lys Ser Gln Phe Glu Gly
         80                  85                  90 ttt gtg aag gat ata atg tta aac aaa gag gag acg aag aaa gaa aac        399
Phe Val Lys Asp Ile Met Leu Asn Lys Glu Glu Thr Lys Lys Glu Asn
     95                 100                 105 agc ttt gaa atg caa aaa ggt gat cag aat cct caa att gcg gca cat        447
Ser Phe Glu Met Gln Lys Gly Asp Gln Asn Pro Gln Ile Ala Ala His
110                 115                 120                 125 gtc ata agt gag gcc agc agt aaa aca aca tct gtg tta cag tgg gct        495
Val Ile Ser Glu Ala Ser Ser Lys Thr Thr Ser Val Leu Gln Trp Ala
                130                 135                 140 gaa aaa gga tac tac acc atg agc aac aac ttg gta acc ctg gaa aat        543
Glu Lys Gly Tyr Tyr Thr Met Ser Asn Asn Leu Val Thr Leu Glu Asn
            145                 150                 155 ggg aaa cag ctg acc gtt aaa aga caa gga ctc tat tat atc tat gcc        591
Gly Lys Gln Leu Thr Val Lys Arg Gln Gly Leu Tyr Tyr Ile Tyr Ala
        160                 165                 170 caa gtc acc ttc tgt tcc aat cgg gaa gct tcg agt caa gct cca ttt        639
Gln Val Thr Phe Cys Ser Asn Arg Glu Ala Ser Ser Gln Ala Pro Phe
    175                 180                 185 ata gcc agc ctc tgc cta aag tcc ccc ggt aga ttc gag aga atc tta        687
Ile Ala Ser Leu Cys Leu Lys Ser Pro Gly Arg Phe Glu Arg Ile Leu
190                 195                 200                 205 ctc aga gct gca aat acc cac agt tcc gcc aaa cct tgc ggg caa caa        735
Leu Arg Ala Ala Asn Thr His Ser Ser Ala Lys Pro Cys Gly Gln Gln
                210                 215                 220 tcc att cac ttg gga gga gta ttt gaa ttg caa cca ggt gct tcg gtg        783
Ser Ile His Leu Gly Gly Val Phe Glu Leu Gln Pro Gly Ala Ser Val
            225                 230                 235 ttt gtc aat gtg act gat cca agc caa gtg agc cat ggc act ggc ttc        831
Phe Val Asn Val Thr Asp Pro Ser Gln Val Ser His Gly Thr Gly Phe
        240                 245                 250
```

```
acg tcc ttt ggc tta ctc aaa ctc tga acagtgtcac cttgcaggct        878
Thr Ser Phe Gly Leu Leu Lys Leu
    255                 260 gtggtggagc tgacgctggg agtcttcata atacagcaca gcggttaagc ccacccctg    938
ttaactgcct atttataacc ctaggatcct ccttatggag aactatttat tatacactcc    998
aaggcatgta gaactgtaat aagtgaatta caggtcacat gaaaccaaaa cgggccctgc   1058
tccataagag cttatatatc tgaagcagca accccactga tgcagacatc cagagagtcc   1118
tatgaaaaga caaggccatt atgcacaggt tgaattctga gtaaacagca gataacttgc   1178
caagttcagt tttgtttctt tgcgtgcagt gtctttccat ggataatgca tttgatttat   1238
cagtgaagat gcagaaggga aatggggagc ctcagctcac attcagttat ggttgactct   1298
gggttcctat ggccttgttg gagggggcca ggctctagaa cgtctaacac agtggagaac   1358
cgaaaccccc ccccccgcc accctctcgg acagttattc attctctttc aatctctctc    1418
tctccatctc tctctttcag tctctctctc tcaacctctt tcttccaatc tctctttctc   1478
aatctctctg tttcccttctg tcagtctctt ccctccccca gtctctcttc tcaatccccc   1538
tttctaacac acacacacac acacacacac acacacacac acacacacag               1598
agtcaggccg ttgctagtca gttctcttct ttccaccctg tccctatctc taccactata   1658
gatgagggtg aggagtaggg agtgcagccc tgagcctgcc cactcctcat tacgaaatga   1718
ctgtatttaa aggaaatcta ttgtatctac ctgcagtctc cattgtttcc agagtgaact   1778
tgtaattatc ttgttattta tttttttgaat aataaagacc tcttaacatt aagaaaaaaa   1838
aaaaaaaaaa aaaaaaaaaa a                                             1859
```

<210> SEQ ID NO 23
<211> LENGTH: 261
<212> TYPE: PRT
<213> ORGANISM: Homo sapiens

<400> SEQUENCE: 23

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175
```

```
Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 24
<211> LENGTH: 1192
<212> TYPE: DNA
<213> ORGANISM: Camelus dromedarius
<220> FEATURE:
<221> NAME/KEY: CDS
<222> LOCATION: (71)..(856)
<223> OTHER INFORMATION: PREDICTED: Camelus dromedarius CD40 ligand
      (CD40LG), mRNA NCBI Reference Sequence: XM_010994864.1

<400> SEQUENCE: 24
tttgacagtc ttctcatgct gcctctggca ccttctcggt cagaagacat cacttcaact      60
ctaacacagc atg atc gaa acg tac agc caa cct tct cct cgc tct gtg        109
           Met Ile Glu Thr Tyr Ser Gln Pro Ser Pro Arg Ser Val
             1               5                  10 acc act gga cca ccc gtc agt atg aaa att ttt atg tat tta ctt aca       157
Thr Thr Gly Pro Pro Val Ser Met Lys Ile Phe Met Tyr Leu Leu Thr
     15                  20                  25 gtt ttt ctt atc acc cag atg att ggg tca gca ctg ttt gct gtg tat       205
Val Phe Leu Ile Thr Gln Met Ile Gly Ser Ala Leu Phe Ala Val Tyr
 30                  35                  40                  45 ctt cac aga aga ttg gac aag ata gaa gat gaa agg aat ctt cat gaa       253
Leu His Arg Arg Leu Asp Lys Ile Glu Asp Glu Arg Asn Leu His Glu
             50                  55                  60 gat ttt gtg ttc atg aaa acg ata cag aga tgc aac aaa gga gag ggg       301
Asp Phe Val Phe Met Lys Thr Ile Gln Arg Cys Asn Lys Gly Glu Gly
         65                  70                  75 tcc tta tct tta ctg aat tgt gag gaa att aga agc cag ttt gaa gac       349
Ser Leu Ser Leu Leu Asn Cys Glu Glu Ile Arg Ser Gln Phe Glu Asp
     80                  85                  90 ctg gtc aag gat ata atg caa agc aaa gaa gtg aag aag aaa gaa aat       397
Leu Val Lys Asp Ile Met Gln Ser Lys Glu Val Lys Lys Lys Glu Asn
 95                 100                 105 aac ttt gaa atg cac aaa ggt gat cag gag cct caa atc gcg gcc cac       445
Asn Phe Glu Met His Lys Gly Asp Gln Glu Pro Gln Ile Ala Ala His
110                 115                 120                 125 gtc atc agt gag gcc agc agt aaa aca gca tct gtt cta cag tgg gcc       493
Val Ile Ser Glu Ala Ser Ser Lys Thr Ala Ser Val Leu Gln Trp Ala
            130                 135                 140 ccc aaa gga tac tac acc cta agc agc aac ttg gtc acc ctg gaa aac       541
Pro Lys Gly Tyr Tyr Thr Leu Ser Ser Asn Leu Val Thr Leu Glu Asn
        145                 150                 155 ggg aaa caa ctg gcc gtt aaa aga caa gga ctc tat tac atc tac gcc       589
Gly Lys Gln Leu Ala Val Lys Arg Gln Gly Leu Tyr Tyr Ile Tyr Ala
        160                 165                 170 caa gtc acc ttc tgt tcc aat cga gaa gct ttg aat caa gcg cct ttc       637
Gln Val Thr Phe Cys Ser Asn Arg Glu Ala Leu Asn Gln Ala Pro Phe
```

-continued

```
                175                 180                 185
ata gcc agc ctc tgc ctg agg tcc aca ggt gga tcg gag aga atc tta      685
Ile Ala Ser Leu Cys Leu Arg Ser Thr Gly Gly Ser Glu Arg Ile Leu
190             195                 200                 205 ctc aga gct gca aac acc cac agt tcc tcc aaa cct tgc ggg cag caa      733
Leu Arg Ala Ala Asn Thr His Ser Ser Ser Lys Pro Cys Gly Gln Gln
            210                 215                 220 tcc att cac ttg gga gga gtc ttc gaa ttg caa gcc ggt gct tcg gtg      781
Ser Ile His Leu Gly Gly Val Phe Glu Leu Gln Ala Gly Ala Ser Val
        225                 230                 235 ttt gtc aac gtg act gat ccg agc caa gtg agc cac ggg aca ggc ttc      829
Phe Val Asn Val Thr Asp Pro Ser Gln Val Ser His Gly Thr Gly Phe
    240                 245                 250 acg tct ttc ggc tta ctc aaa ctc tga ccggtgtaag ctggcaggct            876
Thr Ser Phe Gly Leu Leu Lys Leu
    255                 260 gtggctgggc tgatgctggc agccttcacc atacagcaaa gcagttagga ccaccccctg    936
ttgaactgcc tatttataat cccaggaccc tcctcatgga aaactattta ttatacatcc    996
cgaggcatgt agggctgcaa tgagtgactt atgggacagg tgagacccaa acaggccctg    1056
ttccttaaga gcttatagtc cgaagcggca gccccactgt gcagacacc cggagagtcc     1116 tatgaaatga cgaggccatt gcacacaggt tgaattctga gtaaacagca gaaaattagc    1176
caagtttagt tgtgtt                                                    1192

<210> SEQ ID NO 25
<211> LENGTH: 261
<212> TYPE: PRT
<213> ORGANISM: Camelus dromedarius

<400> SEQUENCE: 25

Met Ile Glu Thr Tyr Ser Gln Pro Ser Pro Arg Ser Val Thr Thr Gly
1               5                   10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Lys Gly Glu Gly Ser Leu Ser
65                  70                  75                  80

Leu Leu Asn Cys Glu Glu Ile Arg Ser Gln Phe Glu Asp Leu Val Lys
                85                  90                  95

Asp Ile Met Gln Ser Lys Glu Val Lys Lys Lys Glu Asn Asn Phe Glu
            100                 105                 110

Met His Lys Gly Asp Gln Glu Pro Gln Ile Ala Ala His Val Ile Ser
        115                 120                 125

Glu Ala Ser Ser Lys Thr Ala Ser Val Leu Gln Trp Ala Pro Lys Gly
    130                 135                 140

Tyr Tyr Thr Leu Ser Ser Asn Leu Val Thr Leu Glu Asn Gly Lys Gln
145                 150                 155                 160

Leu Ala Val Lys Arg Gln Gly Leu Tyr Tyr Ile Tyr Ala Gln Val Thr
                165                 170                 175

Phe Cys Ser Asn Arg Glu Ala Leu Asn Gln Ala Pro Phe Ile Ala Ser
            180                 185                 190

Leu Cys Leu Arg Ser Thr Gly Gly Ser Glu Arg Ile Leu Leu Arg Ala
```

```
                195                 200                 205
Ala Asn Thr His Ser Ser Lys Pro Cys Gly Gln Gln Ser Ile His
    210                 215                 220

Leu Gly Gly Val Phe Glu Leu Gln Ala Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
        260

<210> SEQ ID NO 26
<211> LENGTH: 1203
<212> TYPE: DNA
<213> ORGANISM: Camelus bactrianus
<220> FEATURE:
<221> NAME/KEY: CDS
<222> LOCATION: (71)..(856)
<223> OTHER INFORMATION: PREDICTED: Camelus bactrianus CD40 ligand
      (CD40LG), mRNA NCBI Reference Sequence: XM_010952519.1

<400> SEQUENCE: 26
tttgacagtc ttctcatgct gcctctggca ccttctcggt cagaagacat cacttcaact      60
ctaacacagc atg atc gaa acg tac agc caa cct tct cct cgc tct gtg     109
           Met Ile Glu Thr Tyr Ser Gln Pro Ser Pro Arg Ser Val
               1               5                   10 acc act gga cca ccc gtc agt atg aaa att ttt atg tat tta ctt aca     157
Thr Thr Gly Pro Pro Val Ser Met Lys Ile Phe Met Tyr Leu Leu Thr
    15                  20                  25 gtt ttt ctt atc acc cag atg att ggg tca gca ctg ttt gct gtg tat     205
Val Phe Leu Ile Thr Gln Met Ile Gly Ser Ala Leu Phe Ala Val Tyr
30                  35                  40                  45 ctt cac aga aga ttg gac aag ata gaa gat gaa agg aat ctt cat gaa     253
Leu His Arg Arg Leu Asp Lys Ile Glu Asp Glu Arg Asn Leu His Glu
                50                  55                  60 gat ttt gtg ttc atg aaa acg ata cag aga tgc aac aaa gga gag ggg     301
Asp Phe Val Phe Met Lys Thr Ile Gln Arg Cys Asn Lys Gly Glu Gly
            65                  70                  75 tcc tta tct tta ctg aat tgt gag aaa aat aga agc cag ttt gaa gac     349
Ser Leu Ser Leu Leu Asn Cys Glu Lys Asn Arg Ser Gln Phe Glu Asp
        80                  85                  90 ctg gtc aag gat ata atg caa agc aaa gaa gtg aag aag aaa gaa aat     397
Leu Val Lys Asp Ile Met Gln Ser Lys Glu Val Lys Lys Lys Glu Asn
    95                  100                 105 aac ttt gaa atg cac aaa ggt gat cag gag cct caa atc gcg gcc cac     445
Asn Phe Glu Met His Lys Gly Asp Gln Glu Pro Gln Ile Ala Ala His
110                 115                 120                 125 gtc atc agt gag gcc agc agt aaa aca gca tct gtt cta cag tgg gcc     493
Val Ile Ser Glu Ala Ser Ser Lys Thr Ala Ser Val Leu Gln Trp Ala
                130                 135                 140 ccc aaa gga tac tac acc cta agc agc aac ttg gtc acc ctg gaa aac     541
Pro Lys Gly Tyr Tyr Thr Leu Ser Ser Asn Leu Val Thr Leu Glu Asn
            145                 150                 155 ggg aaa caa ctg gcc gtt aaa aga caa gga ctc tat tac atc tac gcc     589
Gly Lys Gln Leu Ala Val Lys Arg Gln Gly Leu Tyr Tyr Ile Tyr Ala
        160                 165                 170 caa gtc acc ttc tgt tcc aat cga gaa gct ttg aat caa gtg cct ttc     637
Gln Val Thr Phe Cys Ser Asn Arg Glu Ala Leu Asn Gln Val Pro Phe
    175                 180                 185 ata gcc agc ctc tgc ctg agg tcc aca ggt gga tcg gag aga atc tta     685
Ile Ala Ser Leu Cys Leu Arg Ser Thr Gly Gly Ser Glu Arg Ile Leu
190                 195                 200                 205
```

```
                                                                        -continued 190             195             200             205 ctc aga gct gca aac acc cac agt tcc tcc aaa cct tgc ggg cag caa         733
Leu Arg Ala Ala Asn Thr His Ser Ser Ser Lys Pro Cys Gly Gln Gln
            210                 215                 220 tcc att cac ttg gga gga gtc ttc gaa ttg caa gcc ggt gct tcg gtg         781
Ser Ile His Leu Gly Gly Val Phe Glu Leu Gln Ala Gly Ala Ser Val
        225                 230                 235 ttt gtc aac gtg act gat ccg agc caa gtg agc cac ggg acg ggc ttc         829
Phe Val Asn Val Thr Asp Pro Ser Gln Val Ser His Gly Thr Gly Phe
    240                 245                 250 acg tct ttc ggc tta ctc aaa ctc tga ccggtgtaag ctggcaggct               876
Thr Ser Phe Gly Leu Leu Lys Leu
    255                 260 gtggctgggc tgatgctggc agccttcacc atacagcaaa gcagttagga ccaccccctg       936
ttgaactgcc tatttataat cccaggaccc tcctcatgga aaactattta ttatacatcc       996
cgaggcatgt agggctgcaa tgagtgactt atgggacagg tgagacccaa acaggccctg      1056
ttccttaaga gcttatagtc cgaagcggca gccccactga tgcagacacc cggagagtcc      1116
tatgaaatga cgaggccatt gcacacaggt tgaattctga gtaaacagca gaaaattagc      1176
caagtttagt tgtgtttctt tgcatgc                                          1203

<210> SEQ ID NO 27
<211> LENGTH: 261
<212> TYPE: PRT
<213> ORGANISM: Camelus bactrianus

<400> SEQUENCE: 27

Met Ile Glu Thr Tyr Ser Gln Pro Ser Pro Arg Ser Val Thr Thr Gly
1               5                   10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Lys Gly Glu Gly Ser Leu Ser
65                  70                  75                  80

Leu Leu Asn Cys Glu Lys Asn Arg Ser Gln Phe Glu Asp Leu Val Lys
                85                  90                  95

Asp Ile Met Gln Ser Lys Glu Val Lys Lys Glu Asn Asn Phe Glu
            100                 105                 110

Met His Lys Gly Asp Gln Glu Pro Gln Ile Ala Ala His Val Ile Ser
        115                 120                 125

Glu Ala Ser Ser Lys Thr Ala Ser Val Leu Gln Trp Ala Pro Lys Gly
    130                 135                 140

Tyr Tyr Thr Leu Ser Ser Asn Leu Val Thr Leu Glu Asn Gly Lys Gln
145                 150                 155                 160

Leu Ala Val Lys Arg Gln Gly Leu Tyr Tyr Ile Tyr Ala Gln Val Thr
                165                 170                 175

Phe Cys Ser Asn Arg Glu Ala Leu Asn Gln Val Pro Phe Ile Ala Ser
            180                 185                 190

Leu Cys Leu Arg Ser Thr Gly Gly Ser Glu Arg Ile Leu Leu Arg Ala
        195                 200                 205

Ala Asn Thr His Ser Ser Ser Lys Pro Cys Gly Gln Gln Ser Ile His
    210                 215                 220
```

```
Leu Gly Gly Val Phe Glu Leu Gln Ala Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```